United States Patent
Chang et al.

(10) Patent No.: US 7,514,567 B2
(45) Date of Patent: Apr. 7, 2009

(54) OXAZOLIDINONE NICOTINIC ACETYLCHOLINE RECEPTOR AGONISTS

(75) Inventors: Hui-Fang Chang, Wilmington, DE (US); Eifion Phillips, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 262 days.

(21) Appl. No.: 10/563,271

(22) PCT Filed: Jul. 6, 2004

(86) PCT No.: PCT/GB2004/002904

§ 371 (c)(1),
(2), (4) Date: Jan. 4, 2006

(87) PCT Pub. No.: WO2005/005435

PCT Pub. Date: Jan. 20, 2005

(65) Prior Publication Data

US 2006/0154945 A1    Jul. 13, 2006

Related U.S. Application Data

(60) Provisional application No. 60/485,523, filed on Jul. 8, 2003.

(51) Int. Cl.
*A61K 31/421* (2006.01)
*A61K 31/422* (2006.01)
*A61K 31/424* (2006.01)
*C07D 413/02* (2006.01)
*C07D 498/10* (2006.01)

(52) U.S. Cl. ........................ 548/216; 514/376
(58) Field of Classification Search ........................ None
See application file for complete search history.

(56) References Cited

U.S. PATENT DOCUMENTS

| 4,855,290 A | 8/1989 | Fisher et al. |
| 5,902,814 A * | 5/1999 | Gordon et al. ............... 514/278 |
| 6,051,581 A | 4/2000 | Gordon et al. |

FOREIGN PATENT DOCUMENTS

WO    0166546 A1    9/2001

WO    WO 01/66546 A    9/2001

OTHER PUBLICATIONS

Merriam-Webster's College Dictionary, Tenth Edition, published 1998 by Merriam-Webster, Incorporated, pp. 924 and 935.*
Bylund et al., "Radioligand saturation binding experiments over large concentration ranges" Life Sciences (2000) vol. 67, pp. 2897-2911.*
Holladay et al., "Neuronal Nicotinic Acid Receptors as Targets for Drug Discovery" Journal of Medicinal Chemistry (1997) vol. 40, No. 26, pp. 4169-4194.*
Database WPI, Derwent Public, London, GB; 2001, XP002304956, Database accession No. 2001-607404, Abstract.
Mullen G., et al, "(−)-Spiroliazabicyclo2.2 . . . Acetylcholine Receptor", Jr. of Medicinal Chem, American Chem Society, vol. 43, No. 22, 2000, pp. 4045-4050, XP002940689.
McDonald et al., (1995) "Nicotinic Acetylcholine Receptors: Molecular Biology, Chemistry and Pharmacology", Chapter 5 in Annual Reports in Medicinal Chemistry, vol. 30, pp. 41-50, Academic Press Inc., San Diego, CA.
Williams et al., (1994) "Neuronal Nicotinic Acetylcholine Receptors," Drug News & Perspectives, vol. 7, pp. 205-223.
Holladay et al. (1997) "Neuronal Nicotinic Acetylcholine Receptors as Targets for Drug Discovery", J. Med. Chem. 40 (26), 4169-4194.
Arneric and Brioni (Eds.) (1998) "Neuronal Nicotinic Receptors: Pharmacology and Therapeutic Opportunities", John Wiley & Sons, New York.
Levin (Ed.) (2001) "Nicotinic Receptors in the Nervous System" CRC Press.
D.B. Bylund, L.C. Murrin, (2000) "Radioligand Saturation Binding Experiments over Large Concentration Ranges", Life Sciences 67, pp. 2897-2911.

* cited by examiner

*Primary Examiner*—Shaojia Anna Jiang
*Assistant Examiner*—Eric S Olson
(74) *Attorney, Agent, or Firm*—Kenneth F. Mitchell

(57) ABSTRACT

Compounds of formula I:

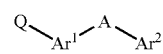

and pharmaceutically-acceptable salts thereof, wherein Q, $Ar^1$, A and $Ar^2$ are as defined in the specification, pharmaceutical compositions and formulations containing them, methods of using them to treat diseases and conditions either alone or in combination with other therapeutically-active compounds or substances, processes and intermediates used to prepare them, uses of them as medicaments for therapy, uses of them in the manufacture of medicaments and uses of them for diagnostic and analytic purposes.

18 Claims, No Drawings

OXAZOLIDINONE NICOTINIC ACETYLCHOLINE RECEPTOR AGONISTS

This is a National Phase filing of International Application No. PCT/GB2004/002904, filed Jul. 6, 2004, which claims the priority of Provisional Application No. 60/485,523 filed in The U.S.A. on July 8, 2003.

TECHNICAL FIELD

This invention relates to novel spiroazabicyclic compounds or pharmaceutically acceptable salts thereof, processes for preparing them, pharmaceutical compositions containing them and their use in therapy.

BACKGROUND OF THE INVENTION

The use of compounds which bind to nicotinic acetylcholine receptors for the treatment of a range of disorders involving reduced cholinergic function such as Alzheimer's disease, cognitive or attention disorders, anxiety, depression, smoking cessation, neuroprotection, schizophrenia, analgesia, Tourette's syndrome, and Parkinson's disease is discussed in: McDonald et al., (1995) "Nicotinic Acetylcholine Receptors: Molecular Biology, Chemistry and Pharmacology", Chapter 5 in Annual Reports in Medicinal Chemistry, vol. 30, pp. 41-50, Academic Press Inc., San Diego, Calif.; Williams et al., (1994) "Neuronal Nicotinic Acetylcholine Receptors," Drug News & Perspectives, vol. 7, pp. 205-223; Holladay et al. (1997) *J. Med. Chem.* 40(26), 4169-4194; Arneric and Brioni (Eds.) (1998) "Neuronal Nicotinic Receptors: Pharmacology and Therapeutic Opportunities", John Wiley & Sons, New York; Levin (Ed.) (2001) "Nicotinic Receptors in the Nervous System" CRC Press.

SUMMARY OF THE INVENTION

This invention encompasses nicotinic acetylcholine receptor-reactive compounds that are ligands for nicotinic acetylcholine receptors in accord with formula I:

Compounds of the invention (nAChRs) in accord with formula I:

$$Q-Ar^1-A-Ar^2;$$     I and pharmaceutically-acceptable salts thereof, wherein:

Q is a moiety of formula II

II

-A- is selected from —O—, —S—, or —NR$^1$—, or is a bond directly connecting Ar$^1$ and Ar$^2$;

Ar$^1$ is selected from formula III or IV:

III

IV wherein B is O, S, or NR$^1$;

R$^1$ is independently at each occurrence selected from hydrogen or R$^3$;

D is independently at each occurrence selected from N or CR$^2$, provided that D is N at no more than two occurrences;

R$^2$ is independently at each occurrence selected from hydrogen, —R$^3$, —C$_2$-C$_6$alkenyl, —C$_2$-C$_6$alkynyl, halogen, —CN, —NO$_2$, —C(O)R$^4$, —S(O)$_n$R$^5$, —NR$^6$R$^7$, —OR$^8$, Q or a bond, provided that R$^2$ is Q at one occurrence, and at one occurrence is a bond connecting Ar$^1$ to A, or when -A- is a bond, to Ar$^2$;

R$^3$ is selected from an unsubstituted straight-chained, branched, or cyclic C$_1$-C$_6$alkyl group, or selected from a straight-chained, branched, or cyclic C$_1$-C$_6$alkyl group substituted with up to five halogen atoms, and up to two substituents selected from: C$_2$-C$_6$alkenyl, C$_2$-C$_6$alkynyl, —CN, —C(O)R$^4$, —S(O)$_n$R$^5$, —NR$^6$R$^7$, or —OR$^8$;

R$^4$ is independently at each occurrence selected from hydrogen, R$^9$, —NR$^{10}$R$^{11}$, or —OR$^8$;

R$^5$ is independently at each occurrence selected from hydrogen, R$^9$, or —NR$^{10}$R$^{11}$;

R$^6$ and R$^7$ are independently at each occurrence selected from hydrogen, R$^9$, —C(O)R$^4$ or —S(O)$_n$R$^5$, or in combination at any one occurrence of —NR$^6$R$^7$ are (CH$_2$)$_p$G(CH$_2$)$_q$ where G is O, S, NR$^8$ or a bond;

R$^8$ is selected from hydrogen or R$^9$;

R$^9$ is selected from an unsubstituted straight-chained, branched, or cyclic C$_1$-C$_6$alkyl group, or selected from a straight-chained, branched, or cyclic C$_1$-C$_6$alkyl group substituted with up to five halogen atoms, and up to one substituent selected from: C$_2$-C$_6$ alkenyl, C$_2$-C$_6$ alkynyl, —CN, —NR$^{10}$R$^{11}$—OR$^{12}$;

R$^{10}$ and R$^{11}$ are independently at each occurrence selected from hydrogen, R$^{12}$, —C(O)R$^{12}$, —S(O)$_n$R$^{12}$, or in combination at any one occurrence of —NR$^{10}$R$^{11}$ are (CH$_2$)$_p$J (CH$_2$)$_q$ where J is O, S, NH, NR$^{12}$ or a bond;

R$^{12}$ is selected from an unsubstituted straight-chained, branched, or cyclic C$_1$-C$_6$alkyl group, or selected from a straight-chained, branched, or cyclic C$_1$-C$_6$alkyl group substituted with up to five halogen atoms;

Ar$^2$ is selected from an unsubstituted 5- or 6-membered aromatic or heteroaromatic ring containing zero to two nitrogen atoms, zero to one oxygen atoms, and zero to one sulfur atoms, or selected from an 8-, 9- or 10-membered fused aromatic or heteroaromatic ring system containing zero to three nitrogen atoms, zero to one oxygen atom, and zero to one sulfur atom, or is selected from a 5- or 6-membered aromatic or heteroaromatic ring containing zero to two nitrogen atoms, zero to one oxygen atoms, and zero to one sulfur atoms, or is selected from an 8-, 9- or 10-membered fused aromatic or heteroaromatic ring system containing zero to three nitrogen atoms, zero to one oxygen atom, and zero to one sulfur atom where each foregoing Ar$^2$ moiety may bear one to three substituents selected from R$^3$, C$_2$-C$_6$alkenyl, C$_2$-C$_6$alkynyl, halogen, —CN, —NO$_2$, —C(O)R$^4$, —S(O)$_n$R$^5$, —NR$^6$R$^7$, —OR$^8$;

n at each occurrence is 0, 1, or 2;
p at each occurrence is 2, 3, or 4;
q at each occurrence is 0, 1, or 2.

The invention also encompasses stereoisomers, enantiomers, in vivo-hydrolysable precursors and pharmaceutically-acceptable salts of compounds of formula I, pharmaceutical compositions and formulations containing them, methods of using them to treat diseases and conditions either alone or in combination with other therapeutically-active compounds or substances, processes and intermediates used to prepare them, uses of them as medicaments, uses of them in the manufacture of medicaments and uses of them for diagnostic and analytic purposes.

DESCRIPTION OF THE INVENTION

Compounds of the invention are ligands for nicotinic acetylcholine receptors (nAChRs) in accord with formula I:

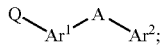
I and pharmaceutically-acceptable salts thereof, wherein:
Q is a moiety of formula II

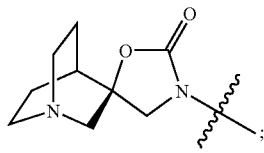
II

-A- is selected from —O—, —S—, or —NR$^1$—, or is a bond directly connecting Ar$^1$ and Ar$^2$;
Ar$^1$ is selected from formula III or IV:

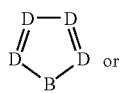
III

IV wherein B is O, S, or NR$^1$;
R$^1$ is independently at each occurrence selected from hydrogen or R$^3$;
D is independently at each occurrence selected from N or CR$^2$, provided that D is N at no more than two occurrences;
R$^2$ is independently at each occurrence selected from hydrogen, —R$^3$, —C$_2$-C$_6$alkenyl, —C$_2$-C$_6$alkynyl, halogen, —CN, —NO$_2$, —C(O)R$^4$, —S(O)$_n$R$^5$, —NR$^6$R$^7$, —OR$^8$, Q or a bond, provided that R$^2$ is Q at one occurrence, and at one occurrence is a bond connecting Ar$^1$ to A, or when -A- is a bond, to Ar$^2$;
R$^3$ is selected from an unsubstituted straight-chained, branched, or cyclic C$_1$-C$_6$alkyl group, or selected from a straight-chained, branched, or cyclic C$_1$-C$_6$alkyl group substituted with up to five halogen atoms, and up to two substituents selected from: C$_2$-C$_6$alkenyl, C$_2$-C$_6$alkynyl, —CN, —C(O)R$^4$, —S(O)$_n$R$^5$, —NR$^6$R$^7$, or —OR$^8$;

R$^4$ is independently at each occurrence selected from hydrogen, R$^9$, —NR$^{10}$R$^{11}$, or —OR$^8$;
R$^5$ is independently at each occurrence selected from hydrogen, R$^9$, or —NR$^{10}$R$^{11}$;
R$^6$ and R$^7$ are independently at each occurrence selected from hydrogen, R$^9$, —C(O)R$^4$ or —S(O)$_n$R$^5$, or in combination at any one occurrence of —NR$^6$R$^7$ are (CH$_2$)$_p$G(CH$_2$)$_q$ where G is O, S, NR$^8$ or a bond;
R$^8$ is selected from hydrogen or R$^9$;
R$^9$ is selected from an unsubstituted straight-chained, branched, or cyclic C$_1$-C$_6$alkyl group, or selected from a straight-chained, branched, or cyclic C$_1$-C$_6$alkyl group substituted with up to five halogen atoms, and up to one substituent selected from: C$_2$-C$_6$ alkenyl, C$_2$-C$_6$ alkynyl, —CN, —NR$^{10}$R$^{11}$—OR$^{12}$;
R$^{10}$ and R$^{11}$ are independently at each occurrence selected from hydrogen, R$^{12}$, —C(O)R$^{12}$, —S(O)$_n$R$^{12}$, or in combination at any one occurrence of —NR$^{10}$R$^{11}$ are (CH$_2$)$_p$J (CH$_2$)$_q$ where J is O, S, NH, NR$^{12}$ or a bond;
R$^{12}$ is selected from an unsubstituted straight-chained, branched, or cyclic C$_1$-C$_6$alkyl group, or selected from a straight-chained, branched, or cyclic C$_1$-C$_6$alkyl group substituted with up to five halogen atoms;
Ar$^2$ is selected from an unsubstituted 5- or 6-membered aromatic or heteroaromatic ring containing zero to two nitrogen atoms, zero to one oxygen atoms, and zero to one sulfur atoms, or selected from an 8-, 9- or 10-membered fused aromatic or heteroaromatic ring system containing zero to three nitrogen atoms, zero to one oxygen atom, and zero to one sulfur atom, or is selected from a 5- or 6-membered aromatic or heteroaromatic ring containing zero to two nitrogen atoms, zero to one oxygen atoms, and zero to one sulfur atoms, or is selected from an 8-, 9- or 10-membered fused aromatic or heteroaromatic ring system containing zero to three nitrogen atoms, zero to one oxygen atom, and zero to one sulfur atom where each foregoing Ar$^2$ moiety may bear one to three substituents selected from R$^3$, C$_2$-C$_6$alkenyl, C$_2$-C$_6$alkynyl, halogen, —CN, —NO$_2$, —C(O)R$^4$, —S (O)$_n$R$^5$, —NR$^6$R$^7$, —OR$^8$;
n at each occurrence is 0, 1, or 2;
p at each occurrence is 2, 3, or 4;
q at each occurrence is 0, 1, or 2;
stereoisomers, enantiomers, in vivo-hydrolysable precursors and pharmaceutically-acceptable salts thereof.

Particular compounds of the invention are those in accord with formula I wherein:
Ar$^1$ is selected from formula III or IV:

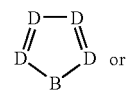
III

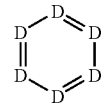
IV

B is O, S, or NR$^1$;
R$^1$ is independently at each occurrence selected from hydrogen or R$^3$;
D is independently at each occurrence selected from N or CR$^2$, provided that D is N at two occurrences;
R$^2$ is independently at each occurrence selected from hydrogen, —R$^3$, halogen, —CN, —NO$_2$, —C(O)R$^4$, —S(O)

$R^5$, —$NR^6R^7$, —$OR^8$, Q or a bond, provided that $R^2$ is Q at one occurrence, and at one occurrence is a bond connecting $Ar^1$ to A, or when -A- is a bond, to $Ar^2$;

$R^3$ is an unsubstituted straight-chained, branched, or cyclic $C_1$-$C_6$alkyl group, or a straight-chained, branched, or cyclic $C_1$-$C_6$alkyl group substituted with up to five halogen atoms, and up to two substituents selected from: —CN, —C(O)$R^4$, —S(O)$_n$$R^5$, —$NR^6R^7$, or —$OR^8$;

$R^4$, $R^5$, $R^6$, $R^7$ and $R^8$ are independently at each occurrence selected from hydrogen or $R^9$;

$R^9$ is selected from an unsubstituted straight-chained, branched, or cyclic $C_1$-$C_6$alkyl group, or is selected from a straight-chained, branched, or cyclic $C_1$-$C_6$alkyl group substituted with up to five halogen atoms, and up to one substituent selected from: —CN, —$NR^{10}R^{11}$—$OR^{12}$;

$R^{10}$ and $R^{11}$ are at each occurrence hydrogen;

$R^{12}$ is selected from an unsubstituted straight-chained, branched, or cyclic $C_1$-$C_6$alkyl group, or selected from a straight-chained, branched, or cyclic $C_1$-$C_6$alkyl group substituted with up to five halogen atoms;

-A- is selected from —O—, —S—, or —$NR^1$—, or is a bond directly connecting $Ar^1$ and $Ar^2$;

$Ar^2$ is selected from unsubstituted phenyl; 2-pyridyl, 3-pyridyl or 4-pyridyl; 2-pyrimidyl, 4-pyrimidyl or 5-pyrimidyl; 2-pyrazinyl or 3-pyrazinyl; 2-furyl or 3-furyl; 2-thiophenyl or 3-thiophenyl; 1-pyrrolyl, 2-pyrrolyl or 3-pyrrolyl; 2-quinazolyl, 4-quinazolyl or 5-quinazolyl; 2-oxazolyl, 4-oxazolyl or 5-oxazolyl; 2-imidazolyl, 4-imidazolyl or 5-imidazolyl; 1-naphthyl or 2-naphthyl; 2-quinolyl, 3-quinolyl, 4-quinolyl, 5-quinolyl, 6-quinolyl, 7-quinolyl or 8-quinolyl; 1-isoquinolyl, 3-isoquinolyl, 4-isoquinolyl; 5-isoquinolyl, 6-isoquinolyl, 7-isoquinolyl or 8-isoquinolyl; 2-benzofuranyl, 3-benzofuranyl, 4-benzofuranyl, 5-benzofuranyl, 6-benzofuranyl or 7-benzofuranyl, 2-benzo[b]thiophenyl, 3-benzo[b]thiophenyl, 4-benzo[b]thiophenyl, 5-benzo[b]thiophenyl, 6-benzo[b]thiophenyl or 7-benzo[b]thiophenyl; 2-indolyl, 3-indolyl, 4-indolyl, 5-indolyl, 6-indolyl or 7-indolyl; 2-benzoxazolyl, 4-benzoxazolyl, 5-benzoxazolyl, 6-benzoxazolyl; or 7-benzoxazolyl; 2-benzthiazolyl, 4-benzthiazolyl, 5-benzthiazolyl, 6-benzthiazolyl or 7-benzthiazolyl; or is selected from any foregoing $Ar^2$ moiety substituted with one to three substituents selected from $R^3$, $C_2$-$C_6$ alkenyl, $C_2$-$C_6$ alkynyl, halogen, —CN, —$NO_2$, —C(O)$R^4$, —S(O)$_n$$R^5$, —$NR^6R^7$, —$OR^8$;

n at each occurrence is 0, 1, or 2.

Other particular compounds of the invention are those wherein $R^2$ is Q at one occurrence and is a bond connecting $Ar^1$ to A at one occurrence and otherwise is hydrogen.

Other particular compounds of the invention are those wherein Q and -A-$Ar^2$ are in a 1,3 relationship with one another on $Ar^1$.

Other particular compounds of the invention are those wherein -A- is a bond directly connecting $Ar^1$ and $Ar^2$.

Still other compounds of the invention are those wherein $Ar^1$ is a moiety of formula III.

Other compounds of the invention are those where $Ar^1$ is a furan ring.

Other compounds of the invention are those where $Ar^1$ is a thiophene ring.

Yet other compounds of the invention are those wherein $Ar^1$ is a moiety of formula III and B is O.

Still other compounds of the invention are those wherein $Ar^1$ is a moiety of formula III and B is S.

Still other compounds of the invention are those wherein $Ar^1$ is a moiety of formula III and D is $CR^2$ where $R^2$ is Q at one occurrence and is a bond connecting $Ar^1$ to A at one occurrence and otherwise is hydrogen.

Other compounds of the inventions are those wherein $R^3$ is selected from:
methyl, ethyl,
linear, cyclic or branched propyl, butyl, pentyl or hexyl,
ethenyl or 1-propenyl, 2-propenyl or 3-propenyl,
linear, branched or cyclic butenyl, pentenyl or hexenyl,
ethynyl or propynyl,
chloro, bromo, fluoro or iodo, —CN, —$NO_2$, —C(O)$R^4$, —S(O)$_n$$R^5$, —$NR^6R^7$ or —$OR^8$;

$R^4$ is independently at each occurrence selected from hydrogen, $R^9$, —$NR^{10}R^{11}$, —$OR^8$; trifluoromethyl, trifluoroethyl, methoxymethyl, trifluoromethoxymethyl, methoxyethyl or trifluoromethoxyethyl;

$R^5$ is independently at each occurrence selected from hydrogen, $R^9$, or —$NR^{10}R^{11}$;

$R^6$ and $R^7$ are independently at each occurrence selected from hydrogen, $R^9$, —C(O)$R^4$, —S(O)$_n$$R^5$, or in combination at any one occurrence of —$NR^6R^7$ are $(CH_2)_pG(CH_2)_q$ where G is O, S, $NR^8$ or a bond;

$R^8$ is selected from hydrogen or $R^9$;

$R^9$ is selected from:
methyl, ethyl,
linear, cyclic or branched propyl, butyl, pentyl or hexyl
ethenyl or 1-propenyl, 2-propenyl or 3-propenyl
linear, branched or cyclic butenyl, pentenyl or hexenyl,
ethynyl or propynyl, where any foregoing $R^9$ moiety may bear up to five chloro, bromo, fluoro, iodo atoms, and up to one substituent selected from:
—CN, —$NR^{10}R^{11}$—$OR^{12}$;

$R^{10}$ and $R^{11}$ are independently at each occurrence selected from hydrogen, $R^{12}$, —C(O)$R^{12}$, —S(O)$_n$$R^{12}$, or in combination at any one occurrence of —$NR^{10}R^{11}$ are $(CH_2)_pJ(CH_2)_q$ where J is O, S, NH, $NR^{12}$ or a bond;

$R^{12}$ is selected from:
methyl, ethyl,
linear, cyclic or branched propyl, butyl, pentyl or hexyl
ethenyl or 1-propenyl, 2-propenyl or 3-propenyl
linear, branched or cyclic butenyl, pentenyl or hexenyl,
ethynyl or propynyl, where any foregoing $R^{12}$ moiety may bear up to five chloro, bromo, fluoro, iodo atoms, $Ar^2$ is selected from unsubstituted phenyl; 2-pyridyl, 3-pyridyl or 4-pyridyl; 2-pyrimidyl, 4-pyrimidyl or 5-pyrimidyl; 2-pyrazinyl or 3-pyrazinyl; 2-furyl or 3-furyl; 2-thiophenyl or 3-thiophenyl; 1-pyrrolyl, 2-pyrrolyl or 3-pyrrolyl; 2-quinazolyl, 4-quinazolyl or 5-quinazolyl; 2-oxazolyl, 4-oxazolyl or 5-oxazolyl; 2-imidazolyl, 4-imidazolyl or 5-imidazolyl; 1-naphthyl or 2-naphthyl; 2-quinolyl, 3-quinolyl, 4-quinolyl, 5-quinolyl, 6-quinolyl, 7-quinolyl or 8-quinolyl; 1-isoquinolyl, 3-isoquinolyl, 4-isoquinolyl; 5-isoquinolyl, 6-isoquinolyl, 7-isoquinolyl or 8-isoquinolyl; 2-benzofuranyl, 3-benzofuranyl, 4-benzofuranyl, 5-benzofuranyl, 6-benzofuranyl or 7-benzofuranyl, 2-benzo[b]thiophenyl, 3-benzo[b]thiophenyl, 4-benzo[b]thiophenyl, 5-benzo[b]thiophenyl, 6-benzo[b]thiophenyl or 7-benzo[b]thiophenyl; 2-indolyl, 3-indolyl, 4-indolyl, 5-indolyl, 6-indolyl or 7-indolyl; 2-benzoxazolyl, 4-benzoxazolyl, 5-benzoxazolyl, 6-benzoxazolyl; or 7-benzoxazolyl; 2-benzthiazolyl, 4-benzthiazolyl, 5-benzthiazolyl, 6-benzthiazolyl or 7-benzthiazolyl; or any foregoing $Ar^2$ moiety substituted with 1, 2 or 3 $R^3$ substituents.

Particular compounds of the invention include:
(R)-3'-(5-phenylthiophen-2-yl)spiro[1-azabicyclo[2.2.2]octan-3,5'-oxazolidin]-2'-one;
(R)-3'-[5-(4-pyridyl)thiophen-2-yl]spiro[1-azabicyclo[2.2.2]octan-3,5'-oxazolidin]-2'-one;

(R)-3'-[5-(3-pyridyl)thiophen-2-yl]spiro[1-azabicyclo [2.2.2]octan-3,5'-oxazolidin]-2'-one, and
(R)-3'-[5-(2-pyridyl)thiophen-2-yl]spiro[1-azabicyclo [2.2.2]octan-3,5'-oxazolidin]-2'-one.

In another aspect the invention relates to compounds according to formula I and their use in therapy and compositions containing them.

In a further aspect the invention relates to compounds according to formula I wherein one or more of the atoms is labeled as a radioisotope of the same element. In a particular form of this aspect of the invention the compound of formula I is labeled with tritium.

Compounds of the invention labeled with tritium are useful for the discovery of novel medicinal compounds which bind to and modulate the activity, by agonism, partial agonism, or antagonism, of the α7 nicotinic acetylcholine receptor. Such tritium labeled compounds may be used in assays that measure the displacement of a such compounds to assess the binding of ligand that bind to α7 nicotinic acetylcholine receptors.

In a particular aspect the invention relates to the use of compounds according to formula I for the therapy of diseases mediated through the action of nicotinic acetylcholine receptors. A more particular aspect of the invention relates to the use of compounds of formula I for the therapy of diseases mediated through the action of α7 nicotinic acetylcholine receptors.

Another aspect of the invention relates to a method of treatment or prophylaxis of human diseases or conditions in which activation of the α7 nicotinic receptor is beneficial which comprises administering a therapeutically effective amount of a compound of the invention.

Another aspect of the invention relates to a method of treatment or prophylaxis of neurological disorders, psychotic disorders or intellectual impairment disorders, which comprises administering a therapeutically effective amount of a compound of the invention.

Another aspect of the invention relates to a method of treatment or prophylaxis, wherein the disorder is Alzheimer's disease, learning deficit, cognition deficit, attention deficit, memory loss, or Attention Deficit Hyperactivity Disorder.

Another aspect of the invention relates to a method of treatment or prophylaxis, wherein the disorder is Parkinson's disease, Huntington's disease, Tourette's syndrome, or neurodegenerative disorders in which there is loss of cholinergic synapses.

Another aspect of the invention relates to a method of treatment or prophylaxis, wherein the disorder is anxiety, schizophrenia or mania or manic depression.

Another aspect of the invention relates to a method of treatment or prophylaxis of jetlag, cessation of smoking, nicotine addiction, craving, pain, and for ulcerative colitis, which comprises administering a therapeutically effective amount of a compound of the invention.

Another aspect of the invention relates to a pharmaceutical composition comprising a compound of the invention and a pharmaceutically-acceptable diluent or carrier.

A further aspect of the invention relates to a pharmaceutical composition for treating or preventing a condition or disorder mentioned herein arising from dysfunction of nicotinic acetylcholine receptor neurotransmission in a mammal, preferably a human, comprising an amount of a compound of formula I, an enantiomer thereof or a pharmaceutically acceptable salt thereof, effective in treating or preventing such disorder or condition and a pharmaceutically acceptable carrier.

Another aspect of the invention relates to use of the pharmaceutical composition of the invention for the treatment of prophylaxis of human diseases or conditions in which activation of the α7 nicotinic receptor is beneficial.

Another aspect of the invention relates to use of the pharmaceutical composition of the invention for the treatment or prophylaxis of neurological disorders, psychotic disorders or intellectual impairment disorders.

Another aspect of the invention relates to use of the pharmaceutical composition of the invention for the treatment or prophylaxis of Alzheimer's disease, learning deficit, cognition deficit, attention deficit, memory loss, Attention Deficit Hyperactivity Disorder, anxiety, schizophrenia, or mania or manic depression, Parkinson's disease, Huntington's disease, Tourette's syndrome, neurodegenerative disorders in which there is loss of cholinergic synapse, jetlag, cessation of smoking, nicotine addiction including that resulting from exposure to products containing nicotine, craving, pain, and for ulcerative colitis.

A further aspect of the invention is the use of a compound according to the invention, an enantiomer thereof or a pharmaceutically acceptable salt thereof, in the manufacture of a medicament for the treatment or prophylaxis of the diseases or conditions mentioned herein.

Another aspect of the invention relates to a use of a compound of the invention in the manufacture of a medicament for the treatment or prophylaxis of human diseases or conditions in which activation of the α7 nicotinic receptor is beneficial.

Another aspect of the invention relates to a use of a compound of the invention in the manufacture of a medicament for the treatment or prophylaxis of neurological disorders, psychotic disorders or intellectual impairment disorders.

Another aspect of the invention relates to the use of a compound of the invention in the manufacture of a medicament for treatment or prophylaxis of Alzheimer's disease, learning deficit, cognition deficit, attention deficit, memory loss or Attention Deficit Hyperactivity Disorder.

Another aspect of the invention relates to the use of a compound of the invention in the manufacture of a medicament for treatment or prophylaxis of anxiety, schizophrenia, or mania or manic depression.

Another aspect of the invention relates to the use of a compound of the invention in the manufacture of a medicament for treatment or prophylaxis of Parkinson's disease, Huntington's disease, Tourette's syndrome, or neurodegenerative disorders in which there is loss of cholinergic synapses.

Another aspect of the invention relates to the use of a compound as described above in the manufacture of a medicament for the treatment or prophylaxis of jetlag, pain, or ulcerative colitis.

Another aspect of the invention relates to the use of a compound of the invention in the manufacture of a medicament for facilitating the cessation of smoking or the treatment of nicotine addiction or craving including that resulting from exposure to products containing nicotine.

For the uses, methods and compositions mentioned herein the dosage administered will, of course, vary with the compound employed, the mode of administration and the treatment desired. However, in general, satisfactory results are obtained when the compounds of the invention are administered at a daily dosage of from about 0.1 mg to about 20 mg/kg of animal body weight. Such doses may be given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carrier or diluent.

The compounds of formula I, an enantiomer thereof, and pharmaceutically acceptable salts thereof, may be used on their own or in the form of appropriate medicinal preparations for enteral or parenteral administration. According to a further aspect of the invention, there is provided a pharmaceutical composition including preferably less than 80% and more preferably less than 50% by weight of a compound of the invention in admixture with an inert pharmaceutically acceptable diluent or carrier.

Examples of diluents and carriers are:
- for tablets and dragees: lactose, starch, talc, stearic acid;
- for capsules: tartaric acid or lactose;
- for injectable solutions: water, alcohols, glycerin, vegetable oils;
- for suppositories: natural or hardened oils or waxes.

There is also provided a process for the preparation of such a pharmaceutical composition which comprises mixing the ingredients.

Compounds according to the invention are agonists of nicotinic acetylcholine receptors. While not being limited by theory, it is believed that agonists of the α7 nAChR (nicotinic acetylcholine receptor) subtype should be useful in the treatment or prophylaxis of neurological disorders, psychotic disorders and intellectual impairment disorders, and have advantages over compounds which are or are also agonists of the α4 nAChR subtype. Therefore, compounds which are selective for the α7 nAChR subtype are preferred. The compounds of the invention are indicated as pharmaceuticals, in particular in the treatment or prophylaxis of neurological disorders, psychotic disorders and intellectual impairment disorders. Examples of psychotic disorders include schizophrenia, mania and manic depression, and anxiety. Examples of intellectual impairment disorders include Alzheimer's disease, learning deficit, cognition deficit, attention deficit, memory loss, and Attention Deficit Hyperactivity Disorder. The compounds of the invention may also be useful as analgesics in the treatment of pain (including chronic pain) and in the treatment or prophylaxis of Parkinson's disease, Huntington's disease, Tourette's syndrome, and neurodegenerative disorders in which there is loss of cholinergic synapses. The compounds may further be indicated for the treatment or prophylaxis of jetlag, for use in inducing the cessation of smoking, craving, and for the treatment or prophylaxis of nicotine addiction (including that resulting from exposure to products containing nicotine).

It is also believed that compounds according to the invention are useful in the treatment and prophylaxis of ulcerative colitis.

As used herein, the term "$C_{1-6}$ alkyl" refers to a straight-chained, branched, or cyclic $C_{1-6}$ alkyl group.

As used herein the term "halogen" refers to fluorine, chlorine, bromine or iodine.

Methods of Preparation

Methods which may be used for the synthesis of compounds of formula I, include methods A, B, C, and D described below. In the methods, unless otherwise indicated, $Ar^1$, $Ar^2$ and A are as defined for formula I.

Method A

Scheme 1

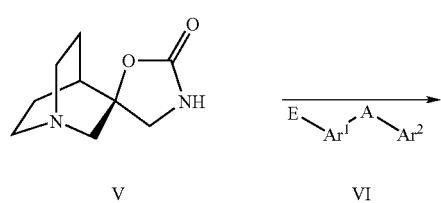

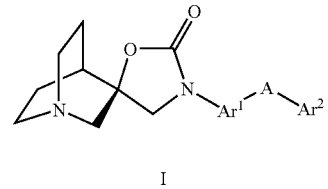

I

In Formula VI of Scheme 1, E represents a moiety $R^2$ in $Ar^1$ which becomes the occurrence of $R^2$ Q in formula I. In Formula VI E is a halogen or an $OSO_2CF_3$ group.

Compounds of formula I may be prepared by treatment of a compound of formula V with a compound of formula VI in the presence of a base. To perform the reaction, the presence of a catalyst, such as an organometallic catalyst may facilitate the reaction, or may be necessary to drive the reaction. Suitable organic bases include lithium, sodium, or potassium bases, including hydrides, alkoxides, hydroxides carbonates, amides, alkylamides, or alkyls. Suitable catalysts include copper, palladium, or nickel compounds. The catalysts may include the metal, salts, or organometallic complexes, either preformed as an organometallic compound or formed in situ by the addition of a ligand. Suitable ligands include diamine ligands such as 1,2-diaminoethane or 1,2-diaminocyclohexane, or phosphine ligands such as triphenylphosphine. The preferred base is potassium carbonate. The preferred catalyst is copper (I) iodide. The reaction is preferably performed in the presence of ethylenediamine as a ligand. The reaction is performed in an inert solvent. The preferred inert solvent is 1,4-dioxane. The reaction performed at a temperature of approximately 100° C.

Method B

Scheme 2

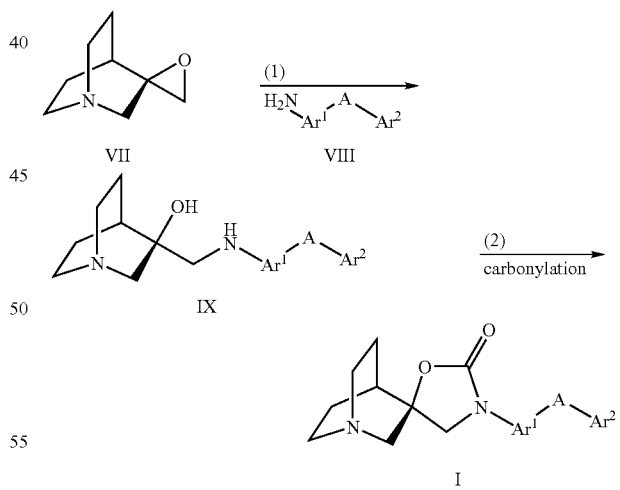

In Formula VIII of Scheme 2, $H_2N$—$Ar^1$ represents a moiety $R^2$ in $Ar^1$ which becomes the occurrence of $R^2$ represented by Q of formula I. Likewise, in formula IX above $Ar^1$ is connected to the nitrogen of the aminoalcohol at position of $Ar^1$ that becomes Q in the compound of formula I.

Method B may be carried out in two steps: ring opening of epoxide VII with compound VIII, followed by carbonylation of the resulting intermediate IX to form the oxazolidinone ring of a compound of formula I.

Compounds of formula IX may be prepared by treatment of a compound of formula VII with a compound of formula VIII. In order to perform the reaction, the presence of a base may facilitate the reaction, and may be necessary to perform the reaction, and it may be desirable or necessary to form an amide anion of compound VIII. Suitable organic bases include alkali metal bases, including hydrides, alkoxides, amides, alkylamides, or alkyls. Preferred bases are strong bases, such as alkyllithium bases, or lithium dialkylamide, or sodium hydride or potassium hydride. The reaction is performed in an inert solvent. The preferred inert solvent is tetrahydrofuran.

Compounds of formula I may be prepared treatment of a compound of formula IX with a carbonyl donating compound. Examples of carbonyl donating compounds include carbonyldiimidazole, carbonyldichloride (phosgene), and triphosgene. The reaction is performed in an inert solvent, for example tetrahydrofuran or toluene. The reaction is performed at elevated temperature, for example, in refluxing tetrahydrofuran or toluene.

Method C propylethylamine. Suitable coupling agents when G is OH include: carbodiimides, for example 1,3-dicyclohexylcarbodiimide or 1-(3-dimethylaminopropyl-3-ethylcarbodiimide hydrochloride; phosphonium reagents, for example benzotriazol-1-yloxytris(dimethylamino)phosphonium hexafluorophosphate or benzotriazol-1-yloxytripyrrolidinophosphonium hexafluorophosphate; and uronium reagents, for example O-benzotriazol-1-yl-N,N,N',N'-tetramethyluronium tetrafluoroborate. The preferred coupling agent is O-benzotriazol-1-yl-N,N,N',N'-tetramethyluronium tetrafluoroborate. Suitable solvents for the reaction include N,N-dimethylformamide, dimethylsulfoxide, tetrahydrofuran, or chloroform. The preferred solvent is N,N-dimethylformamide. The reaction is preferably performed at a temperature of 0-50° C., and most preferably at a temperature of 20-30° C.

The conversion of the amide of formula XI to an amino alcohol of formula IX by reduction of the carbonyl group may be performed by treatment of the amide with a suitable reducing agent in a suitable solvent. Suitable reducing agents

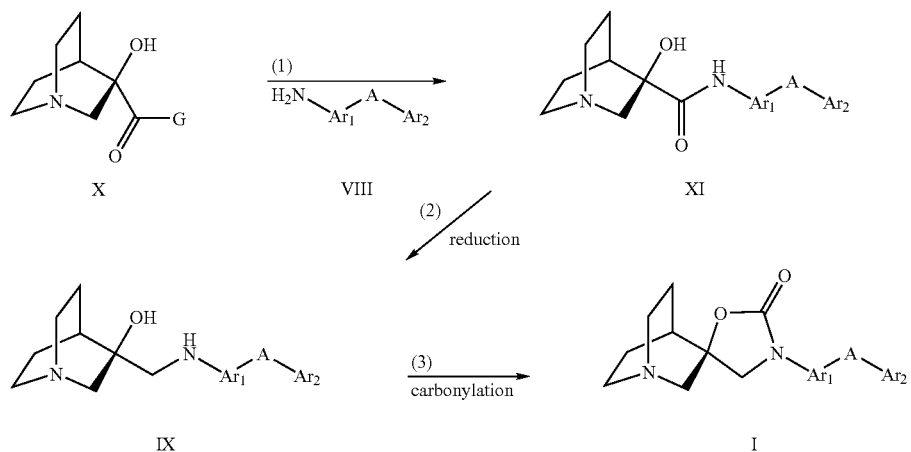

Scheme 3

Method C may be carried out in three steps: amide bond formation between an carboxylic acid derivative of formula X and a compound of formula VIII, reduction of the carbonyl group of the resulting amide of formula XI, in which G is a leaving group, followed by carbonylation of the resulting aminoalcohol of formula VIII to form the oxazolidinone ring of formula IX.

In formula X, $Ar^1$ is connected to an amide nitrogen at the position of $Ar^1$ that will become Q in the compound of formula I. Thus, in formula X $R^2$ is a bond connecting $Ar^1$ and the amide nitrogen.

For the preparation of an amide of formula XI from a compound of formula VIII and a carboxylic acid derivative of formula X, in the compound of formula X, suitable leaving groups G include: OH, halogen, OAlkyl, OAryl, OCOAlkyl, OCOAryl. The reaction is performed by mixing the compounds of formula VIII and XI in a suitable solvent and maintaining the mixture at 0-100° C. The presence of a base, or, when G is OH, a coupling agent, may also be necessary for the reaction to occur. Suitable bases for the reaction include: 4-(N,N-dimethylamino)pyridine, pyridine, triethylamine, N,N-diisopropylethylamine. The preferred base is N,N-diisoinclude aluminium hydride, and lithium aluminium hydride. Suitable solvents include ether solvents, for example tetrahydrofuran.

Compounds of formula I may be prepared treatment of a compound of formula IX with a carbonyl donating compound as described for Method B above.

Method D

Scheme 4

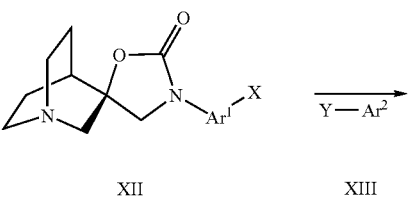

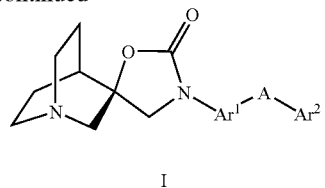

I

In Formula XII of Scheme 4, $Ar^1$—X represents a moiety $OR^2$ in $Ar^1$ where $R^2$ is a bond that becomes connected to the A moiety of a compound of formula I. Thus, in formula XII above, $Ar^1$ is connected to X at the position of $Ar^1$ that is connected to A in the compound of formula I.

(i) A is a Bond

The compounds of formula I wherein A is a bond may be prepared by the cross-coupling reaction of compounds of formula XII and XIII, wherein either X or Y is halogen or $OSO_2CF_3$ when, respectively, Y or X is an organometallic group. Suitable organometallic groups include boronic acid or boronic ester groups, $B(OH)_2$, $B(OR)_2$, or a trialkylstannyl group $SnR_3$, wherein R is an alkyl group. The reaction is performed in the presence of a suitable organometallic catalyst and solvent. Suitable organometallic catalysts include palladium (0) complexes, for example tetrakis(triphenylphosphine)palladium(0) or a combination of tris(dibenzylideneacetone)dipalladium(0) and a suitable triarylphosphine or triarylarsine ligand, for example triphenylphosphine, tri(o-tolyl)phosphine or triphenylarsine. Suitable solvents include inert ether solvents, for example 1,2-dimethoxyethane, tetrahydrofuran, or 1,4-dioxane, or alcohols, such as ethanol, or mixtures thereof. If the compound of formula XI or XII is a boronic acid, the presence of a suitable base in addition to the other reagents is preferred. Suitable bases include sodium carbonate, cesium carbonate, and barium hydroxide. The reaction is carried out at a temperature of 0-120° C., and preferably at a temperature of 60-120° C.

Compounds of formula XII wherein XI is an organometallic group or compounds of formula XIII, wherein either Y is an organometallic group may be prepared from compounds of the corresponding formula wherein X or Y is hydrogen, halogen, or $OSO_2CF_3$ by a suitable metallation or exchange procedure. The compounds wherein the organometallic group is $B(OH)_2$ may be prepared from suitable aromatic compounds having hydrogen or halogen groups, by conversion to the corresponding aryllithium or arylmagnesium compounds followed by reaction with trialkylborate and subsequent hydrolysis of the resulting borate ester. Similarly, compounds wherein the organometallic group is a trialkylstannyl group may be prepared from suitable aromatic compounds having hydrogen or halogen groups, by conversion to the corresponding aryllithium or is arylmagnesium compounds followed by reaction with an appropriate trialkylstannyl halide. The formation of the aryllithium or arylmagnesium compound is performed in a suitable inert solvent, for example, tetrahydrofuran. Alternatively, the compounds wherein the organometallic group is $B(OH)_2$ may be prepared from suitable aromatic compounds having halogen or $OSO_2CF_3$ groups by reaction with bis(pinacolato)diboron and an organometallic catalyst, followed by hydrolysis of the resulting borate ester, compounds wherein the said organometallic group is a trialkylstannyl group may be prepared from suitable aromatic compounds having halogen or $OSO_2CF_3$ groups by reaction with the appropriate bis(trialkyltin) in the presence of a suitable organometallic catalyst. The reaction is performed in a suitable inert solvent, for example tetrahydrofuran, and suitable organometallic catalyst include, for example tetrakis(triphenylphosphine). The reaction is performed at a temperature of about 0° C. to about 150° C., preferably about 20° C. to about 100° C. Typical procedures for effecting such conversions will be known to thoe of skill in the art.

(ii) A is $NR^1$

The compounds of formula I wherein A is a bond may be prepared by the cross-coupling reaction of compounds of formula XII and XIII, wherein either X or Y is halogen or $OSO_2CF_3$ when Y or X, respectively, is $NHR^1$. The reaction may be performed by heating in an inert solvent in the presence of a strong base. Suitable inert solvents include ether solvents, for example tetrahydrofuran, 1,4-dioxane, 1,2-dimethoxyethane, or di(2-methoxyethyl)ether, a hydrocarbon solvent, for example benzene or toluene, or an amide solvent, for example dimethylformamide, or N-methyl-2-pyrrolidinone. The preferred solvent is tetrahydrofuran. Suitable strong bases include alkali metal alkoxide or amide bases, for example sodium t-butoxide or potassium t-butoxide, lithium bis(trimethylsilyl)amide, or lithium diisopropylamide. The preferred strong base is sodium t-butoxide. The reaction may require, and is preferably performed in, the presence of an organometallic catalyst. Suitable organometallic catalysts include complexes of palladium (0) with a suitable phosphine ligand, preferably a triarylphosphine ligand, and most preferably a bidentate triarylphosphine ligand. Preferred ligands include 2,2'-bis(diphenylphosphino)-1,1'-binaphthyl or 1,1'-bis(diphenylphosphino)ferrocene. The catalyst may be synthesised by the combination of a suitable source of palladium (0), for example tris(dibenzylideneacetone)dipalladium (0), with the phosphine ligand, and may either be pre-formed or formed in situ by including the palladium source and phosphine ligand in the reaction mixture. The reaction is carried out at a temperature of about 0-150° C., and preferably at a temperature of about 60-120° C.

(iii) A is O or S

The compounds of formula I wherein A is O or S may be prepared by the cross-coupling reaction of compounds of formula XII and XIII, wherein either X or Y is halogen or $OSO_2CF_3$ where Y or X, respectively is OH or SH. The reaction may be performed by heating in an inert solvent in the presence of a base. The reaction may require, and, when A is O, is preferably performed in, the presence of a catalyst. Suitable inert solvents include ether solvents, for example tetrahydrofuran, 1,4-dioxane, 1,2-dimethoxyethane, or di(2-methoxyethyl)ether, an amide solvent, for example dimethylformamide, or N-methyl-2-pyrrolidinone, or a basic heterocyclic aromatic solvent, for example pyridine. The preferred solvent is pyridine. Suitable bases include alkali metal alkoxides, or alkali metal carbonates, for example potassium carbonate. Suitable organometallic catalysts include copper or its salts, preferably copper (I) salts, and most preferably copper (I) iodide. The reaction is carried out at a temperature of about 0-150° C., and preferably at a temperature of about 100-150° C.

Certain compounds of formula XII wherein X is halogen may be prepared from compounds of formula XII wherein X is hydrogen by reaction with a suitable halogenating agent in a suitable solvent. Suitable halogenating agents include bromine or other elemental halogens. Suitable solvents include acetic acid. The reaction is preferably performed at a temperature of 0-50° C., and most preferably at a temperature of 0-25° C.

Compounds of formula XII wherein X is $OSO_2CF_3$ may be prepared from compounds of formula XII wherein X is OH by reaction with trifluoromethanesulfonic anhydride or other trifluoromethanesulfonylating agent in the presence of a base and a solvent. Suitable bases include pyridine, and 2,6-di-t-butylpyridine. The reaction is preferably performed at a temperature of −78 to 120° C., and most preferably at a temperature of −78 to 0° C.

Certain compounds of formula XII wherein X is hydrogen, halogen, $OSO_2CF_3$, $NHR^1$, OH, or suitable organometallic group may be prepared by procedures analogous to those described under methods A to C above wherein X is substituted for $A$-$Ar^2$ in the formulae represented in the Schemes 1-3.

Compounds of formula XIII in which Y is hydrogen, halogen, $OSO_2CF_3$, $NHR^1$, OH, or suitable organometallic group are commercially available, are described in the literature of synthetic organic chemistry, or may be prepared by methods described herein or known to one skilled in the art of synthetic organic chemistry.

Method E

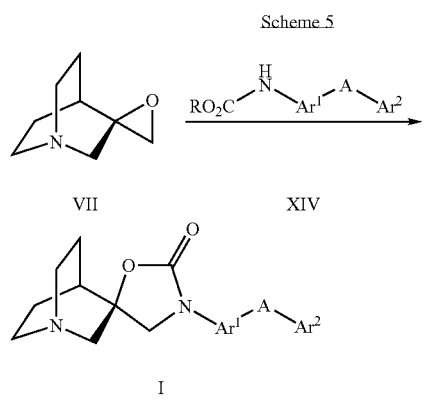

In Formula XIV of Scheme 5, $RO_2CNH$—$Ar^1$ represents a moiety $R^2$ in $Ar^1$ which becomes the occurrence of $R^2$ represented by Q of formula I. R represents an aliphatic or aromatic group such that the moiety $RO_2C$ can act as an intramolecular carbonylating agent with expulsion of OR as a leaving group. Suitable R groups include simple alkyl and aryl groups such as methyl, ethyl, or phenyl. The preferred R group is methyl.

Method E involves a chemical transformation consisting of two reactions: ring opening of epoxide VII with compound XIV, followed by cyclization to form the oxazolidinone ring of a compound of formula I. Method E is analogous to method B except that the group $RO_2C$ in compound XIV rather than a subsequent carbonylation step provides the carbonyl group. The two reactions may be and are preferably performed in a single step whereby VII and XIV are combined in presence of a catalyst. Suitable catalysts include basic catalysts or phase transfer catalysts. The reaction is performed in an inert solvent. The reaction is preferably performed using a phase transfer catalyst such as tetra-n-butylammonium chloride with water as the solvent. The reaction is preferably performed at elevated temperature. For example, when the reaction is performed in water, the reaction is preferably performed at 100° C.

Compounds of formula VI, VIII, and XIV are commercially available, are described in the literature of synthetic organic chemistry, or prepared by methods known to one skilled in the art of synthetic organic chemistry. Compounds may also be prepared from simpler precursors whereby the connection of $Ar^1$ and $Ar^2$ by the linker A is formed by a cross-coupling by methods analogous to those described in method D herein, said precursors being commercially available, described in the literature of synthetic organic chemistry, or prepared by methods known to one skilled in the art of synthetic organic chemistry.

It will be appreciated by one skilled in the art that aromatic substituents in the compounds of the invention, or in intermediates used in the synthesis of compounds of the invention, may be introduced by employing aromatic substitution reactions, functional group transformations to modify existing substituents, or a combination thereof. Such reactions may be effected either prior to or immediately following the processes mentioned above. The reagents and reaction conditions for such procedures are known in the art. Specific examples of procedures which may be employed include, but are not limited to, electrophilic functionalisation of an aromatic ring, for example by nitration, halogenation, or acylation; transformation of a nitro group to an amino group, for example by reduction, such as by catalytic hydrogenation; acylation, alkylation, sulfonylation of an amino or hydroxyl group; replacement of an amino group by another functional group by conversion to an intermediate diazonium salt followed by nucleophilic or free radical substitution of the diazonium salt; or replacement of a halogen by another functional group, for example by nucleophilic or organometallically-catalysed substitution reactions.

Where necessary, hydroxy, amino, or other reactive groups may be protected using protecting groups by standard techniques. The above-described reactions, unless otherwise noted, are usually conducted at a pressure of about one to about three atmospheres, preferably at ambient pressure (about one atmosphere).

Unless otherwise stated, the above-described reactions are conducted under an inert atmosphere, preferably under a nitrogen atmosphere.

The compounds of the invention and intermediates may be isolated from their reaction mixtures by standard techniques.

Acid addition salts of the compounds of formula I which may be mentioned include salts of mineral acids, for example the hydrochloride and hydrobromide salts; and salts formed with organic acids such as formate, acetate, maleate, benzoate, tartrate, and fumarate salts.

Acid addition salts of compounds of formula I may be formed by reacting the free base or a salt, enantiomer or protected derivative thereof, with one or more equivalents of the appropriate acid. The reaction may be carried out in a solvent or medium in which the salt is insoluble or in a solvent in which the salt is soluble, e.g., water, dioxane, ethanol, tetrahydrofuran or diethyl ether, or a mixture of solvents, which may be removed in vacuum or by freeze drying. The reaction may be a metathetical process or it may be carried out on an ion exchange resin.

The compounds of formula I exist in tautomeric or enantiomeric forms, all of which are included within the scope of the invention. The various optical isomers may be isolated by separation of a racemic mixture of the compounds using conventional techniques, e.g. fractional crystallisation, or chiral HPLC. Alternatively the individual enantiomers may be made by reaction of the appropriate optically active starting materials under reaction conditions that will not cause racemisation.

EXAMPLES

Commercial reagents were used without further purification. Mass spectra were recorded using an HPLC-MS system employing a HP-1100 HPLC and a Micromass LCZ Mass Spectrometer using APCI as the ionization technique, and are reported as m/z for the parent molecular ion. Room temperature refers to 20-25° C. (S)-Spiro[1-azabicyclo[2.2.2]octan-3,5'-oxazolidin]-2'-one and other precursors were prepared as described by Mullen et al. (2000) *J. Med. Chem.* 43, 4045-4050. Radio labeled forms of compounds of the examples are useful in a screen for the discovery of novel medicinal compounds that bind to and modulate the activity, by agonism, partial agonism, or antagonism, of the α7 nicotinic acetylcholine receptor. Such radio labeled compounds are synthesized either by incorporating radio labeled starting materials or, in the case of tritium, exchange of hydrogen for tritium by known methods. Known methods include (1) electrophilic halogenation, followed by reduction of the halogen in the presence of a tritium source, for example, by hydrogenation with tritium gas in the presence of a palladium catalyst, or (2) exchange of hydrogen for tritium performed in the presence of tritium gas and a suitable organometallic (e.g. palladium) catalyst.

Preparation 1

(R)-3'-(Thiophen-2-yl)spiro[1-azabicyclo[2.2.2]octan-3,5'-oxazolidin]-2'-one

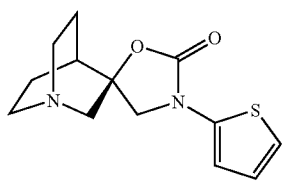

(S)-Spiro[1-azabicyclo[2.2.2]octan-3,5'-oxazolidin]-2'-one (505 mg, 3.58 mmol), 5-bromothiophene (1.75 g, 10.74 mmol), copper (I) iodide (69 mg, 0.36 mmol) and potassium carbonate (495 mg, 3.58 mmol) were stirred at 120° C. overnight. After cooling to room temperature, the mixture was purified by flash chromatography using a gradient of ammoniated methanol in chloroform to give the title compound as a yellow solid (450 mg), m/zz 265 (MH$^+$).

Preparation 2

(R)-3'-(5-Bromothiophen-2-yl)spiro[1-azabicyclo[2.2.2]octan-3,5'-oxazolidin]-2'-one

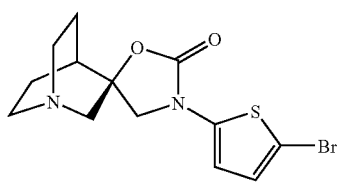

(R)-3'-(Thiophen-2-yl)spiro[1-azabicyclo[2.2.2]octan-3,5'-oxazolidin]-2'-one (425 mg, 1.61 mmol) and N-bromosuccinimide (287 mg, 1.61 mmol) were stirred in DMF (7 mL) at 80° C. for 3 h. The mixture was allowed to cool to room temperature, and was then diluted with chloroform, washed with aqueous potassium carbonate, then with brine, then dried (magnesium sulfate), filtered, and evaporated. The residue was purified by flash chromatography using a gradient of ammoniated methanol in chloroform to give the title compound as a yellow solid as (415 mg), m/zz 343, 345 (MH$^+$).

Preparation 3

(R)-3'-(4-Bromothiophen-2-yl)spiro[1-azabicyclo[2.2.2]octan-3,5'-oxazolidin]-2'-one

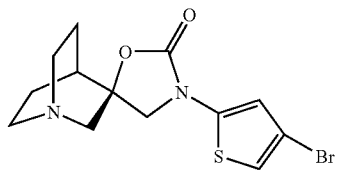

(S)-Spiro[1-azabicyclo[2.2.2]octan-3,5'-oxazolidin]-2'-one (471 mg, 2.58 mmol), 2,4-dibromothiophene (1.875 g, 7.75 mmole), copper (I) iodide (492 mg, 2.58 mmol), potassium carbonate (715 mg, 5.17 mmol) and ethylenediamine (170 µL, 2.58 mmol) in 1,4-dioxane (5 mL) were stirred at 110° C. overnight. The solution was allowed to cool, and then filtered, washed with aqueous ammonium hydroxide and evaporated. The residue was purified by flash chromatography using a gradient of ammoniated methanol in chloroform to give the title compound as a yellow solid (560 mg), m/z 343, 345 (MH$^+$).

Preparation 4

(R)-3'-(Furan-2-yl)spiro[1-azabicyclo[2.2.2]octan-3,5'-oxazolidin]-2'-one

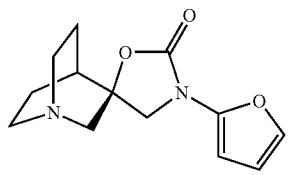

The title compound was prepared by a method analogous to that described in Preparation 3 from (S)-spiro[1-azabicyclo[2.2.2]octan-3,5'-oxazolidin]-2'-one and 2-bromofuran. The title compound (1.49 g) was obtained as a pale-yellow solid, m/z 249 (MH$^+$).

Preparation 5

(R)-3'-(5-Bromofuran-2-yl)spiro[1-azabicyclo[2.2.2]octan-3,5'-oxazolidin]-2'-one

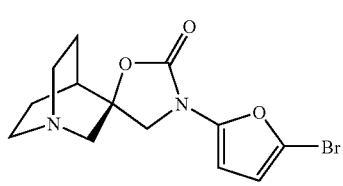

The title compound was prepared by a method analogous to that described in Preparation 2 from (R)-3'-(furan-2-yl)spiro

19

[1-azabicyclo[2.2.2]octan-3,5'-oxazolidin]-2'-one. The title compound (1.70 g) was obtained as a pale-yellow solid, m/z 327, 329 (MH+).

Preparation 6

(R)-3'-[4-Bromo-5-(trimethylsilyl)furan-2-yl]spiro[1-azabicyclo[2.2.2]octan-3,5'-oxazolidin]-2'-one

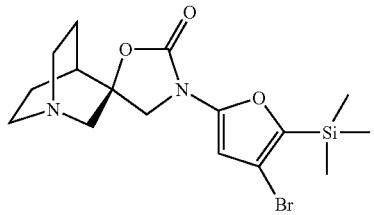

(a) 2,4-Dibromo-5-(trimethylsilyl)furan

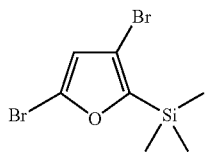

Lithium diisopropylamide (1.8M in heptane/tetrahydrofuran/ethylbenzene, 16.0 mL, 28.8 mmol) was added to a solution of 2,3-dibromofuran (5.0 g, 22.14 mmol) in anhydrous ether (20 mL) that was stirred at −78° C. After 10 min, trimethylsilyl chloride (3.65 mL, 28.8 mmol) was then added at −78° C., then the reaction mixture was allowed to warmed to room temperature, and stirred for another hour. The reaction was quenched with saturated aqueous ammonium chloride then the reaction mixture was partitioned between water and ether. The ether layer was washed with water, then dried (magnesium sulfate), filtered, and the solvent was evaporated. The residue was purified by flash chromatography using hexane to give the sub-title compound as a yellow oil (8.50 g), m/z 297, 299, 301 (MH+). The crude product was used in the next step without further purification.

(b) (R)-3'-[4-Bromo-5-(trimethylsilyl)furan-2-yl]spiro[1-azabicyclo[2.2.2]octan-3,5'-oxazolidin]-2'-one The title compound was prepared by a method analogous to that described in Preparation 3 from (S)-spiro[1-azabicyclo[2.2.2]octan-3,5'-oxazolidin]-2'-one and 2,4-dibromo-5-(trimethylsilyl)furan. The title compound (577 mg) was obtained as a pale yellow solid, m/z 399, 401 (MH+).

Preparation 7

(R)-3'-(4-Bromofuran-2-yl)spiro[1-azabicyclo[2.2.2]octan-3,5'-oxazolidin]-2'-one

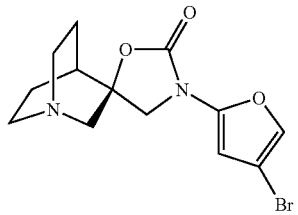

20

Tetra-n-butylammonium fluoride (1M solution in tetrahydrofuran, 2.2 mL, 2.20 mmol) was added to a solution of (R)-3'-[4-bromo-5-(trimethylsilyl)furan-2-yl]spiro[1-azabicyclo[2.2.2]octan-3,5'-oxazolidin]-2'-one (577 mg, 1.44 mmol) in tetrahydrofuran (5 mL). The solution was heated at 70° C. (bath temperature) for 6 h. The reaction mixture was evaporated to dryness, and the residue was subjected to flash chromatography using a gradient of ammoniated methanol in chloroform as the eluant give the title compound as a pale brown solid (387 mg), m/z 327, 329 (MH+).

Preparation 8

3'-(Thiazol-2-yl)spiro[1-azabicyclo[2.2.2]octan-3,5'-oxazolidin]-2'-one

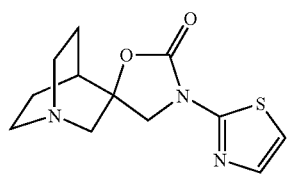

(a) Methyl N-(thiazol-2-yl)carbamate

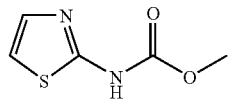

2-Aminothiazole (10.00 g, 99.86 mmole), triethylamine (20.2 g, 200 mmol) and a catalytic amount of 4-(N,N-dimethylamino)pyridine in anhydrous tetrahydrofuran (200 mL) were stirred at 0° C. Methyl chloroformate (18.9 g, 200 mmol) was added slowly to the mixture at 0° C. Then the reaction mixture was stirred at room temperature for several hours. The tetrahydrofuran was evaporated, the residue was dissolved in chloroform, and the resulting solution was washed with water, dried through magnesium sulfate, filtered, and then the solvent was evaporated. The residue was purified by flash chromatography using a gradient of ammoniated methanol in chloroform to give the sub-title compound as a pale yellow solid (17.0 g), m/z 159 (MH+).

(b) 3'-(Thiazol-2-yl)spiro[1-azabicyclo[2.2.2]octan-3,5'-oxazolidin]-2'-one

Spiro[1-azabicyclo[2.2.2]octan-3,2'-oxirane]-N1-trihydroboron (3.00 g, 19.6 mmol), methyl N-(thiazol-2-yl)-carbamate (3.90 g, 23.5 mmol) and tetra-n-butylammonium chloride (1.09 g, 3.92 mmol) were suspended in water (30 mL), and the reaction mixture was stirred at 80° C. overnight. After cooling to room temperature the reaction mixture was filtered, and the collected solid was washed with a small amount of water. The solid was then dissolved in acetone (60 mL), and 6 mL of concentrated hydrochloric acid was added. The mixture was stirred at room temperature overnight. The solvent was evaporated from the mixture, then the residue was partitioned between aqueous potassium carbonate and chloroform. The chloroform layer was dried with magnesium sulphate, filtered and evaporated to give title compound as a pale solid (3.30 g), m/z 266 (MH+).

Preparation 9

3'-(5-Bromothiazol-2-yl)spiro[1-azabicyclo[2.2.2]octan-3,5'-oxazolidin]-2'-one

Method I

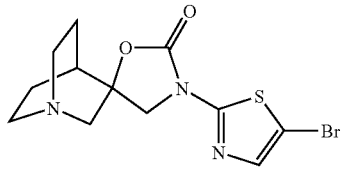

A solution containing 3'-(thiazol-2-yl)spiro[1-azabicyclo[2.2.2]octan-3,5'-oxazolidin]-2'-one (2.80 g, 10.55 mmol) and N-bromosuccinimide (3.90 g, 21.86 mmole) in N,N-dimethylformamide (15 mL) were stirred at RT overnight. The mixture was diluted with chloroform, washed with saturated aqueous potassium carbonate and then with brine, dried through magnesium sulfate, and then the solvent was evaporated. The residue was purified by flash chromatography using a gradient of ammoniated methanol in chloroform to give the title compound as a pale solid (1.70 g), m/z 343, 345 (MH$^+$).

Method II (a) Methyl N-(5-bromothiazol-2-yl)carbamate

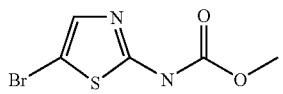

The title compound was prepared by a method analogous to that in Preparation 8(a) from 2-amino-5-bromothiazole. The title compound (4.10 g) was obtained as a yellow solid, m/z 237, 239 (MH$^{30}$).

(b) 3'-(5-Bromothiazol-2-yl)spiro[1-azabicyclo[2.2.2]octan-3,5'-oxazolidin]-2'-one The title compound was prepared by a method analogous to that described in Preparation 8(b) from spiro[1-azabicyclo[2.2.2]octan-3,2'-oxirane]-N1-trihydroboron and methyl N-(5-bromothiazol-2-yl)carbamate. The title compound (650 mg) was obtained as a pale solid, m/z 344, 346 (MH$^+$).

Example 1

(R)-3'-(5-Phenylthiophen-2-yl)spiro[1-azabicyclo[2.2.2]octan-3,5'-oxazolidin]-2'-one

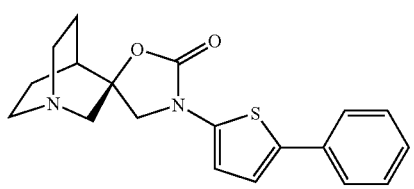

(R)-3'-(5-Bromothiophen-2-yl)spiro[1-azabicyclo[2.2.2]octan-3,5'-oxazolidin]-2'-one (80 mg, 0.23 mmol), phenylboronic acid (31 mg, 0.26 mmol), potassium carbonate (105 mg, 0.76 mmol) and tetrakis(triphenylphosphine)palladium (0) (7 mg, 0.006 mmol) in ethanol/1,2-dimethoxyethane (1:4 v/v; 2 mL) were heated under reflux at 100° C. for 4 h. The solution was allowed to cool, and then filtered and evaporated. Purification by flash chromatography using a gradient of ammoniated methanol in chloroform to give the title compound as a pale-yellow solid (59 mg), m/z 341 (MH$^+$).

Example 2

(R)-3'-[5-(4-Pyridyl)thiophen-2-yl]spiro[1-azabicyclo[2.2.2]octan-3,5'-oxazolidin]-2'-one

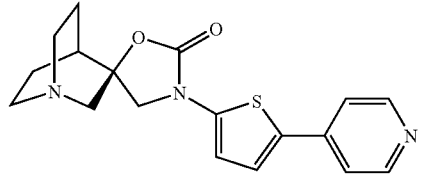

The title compound was prepared by a method analogous to that described in Example 1 from (R)-3'-(5-bromo-thiophen-2-yl)spiro[1-azabicyclo[2.2.2]octan-3,5'-oxazolidin]-2'-one and pyridine-4-boronic acid. The title compound (34 mg) was obtained as a pale-yellow solid, m/z 342 (MH$^+$).

Example 3

(R)-3'-[5-(3-Pyridyl)thiophen-2-yl]spiro[1-azabicyclo[2.2.2]octan-3,5'-oxazolidin]-2'-one

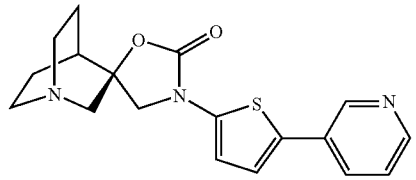

The title compound was prepared by a method analogous to that described in Example 1 from (R)-3'-(5-bromothiophen-2-yl)spiro[1-azabicyclo[2.2.2]octan-3,5'-oxazolidin]-2'-one and pyridine-3-boronic acid. The title compound (24 mg) was isolated as the hydrochloride salt which was an off-white solid, m/z 342 (MH$^+$).

Example 4

(R)-3'-[5-(2-Pyridyl)thiophen-2-yl]spiro[1-azabicyclo[2.2.2]octan-3,5'-oxazolidin]-2'-one

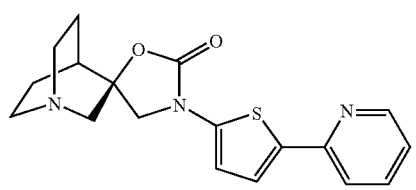

(R)-3'-(5-Bromothiophen-2-yl)spiro[1-azabicyclo[2.2.2]octan-3,5'-oxazolidin]-2'-one 108 mg, 0.31 mmol), 2-tri-n-butylstannylpyridine (218 mg, 0.50 mmol) and tetrakis(triphenylphosphine)palladium (0) (36 mg, 0.03 mmol) were heated in toluene (3.5 mL) 100° C. for 5 h. The solution was filtered, and then subjected to purification by flash chromatography using a gradient of ammoniated methanol in chloroform to give the title compound as a pale solid (73 mg), m/z 342 (MH+).

Example 5

(R)-3'-[5-(Thiophen-2-yl)thiophen-2-yl]spiro[1-azabicyclo[2.2.2]octan-3,5'-oxazolidin]-2'-one

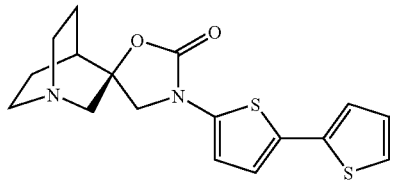

The title compound was prepared by a method analogous to that described in Example 4 from (R)-3'-(5-bromothiophen-2-yl)spiro[1-azabicyclo[2.2.2]octan-3,5'-oxazolidin]-2'-one and 2-(tri-n-butylstannyl)thiophene. The solid obtained from flash chromatography was further purified by reverse phase HPLC on a $C_{18}$ column using a gradient of 5-45% acetonitrile/water (each solvent containing 0.1% trifluoroacetic acid as a buffer) as the eluant. The product-containing fractions were evaporated. The residue was partitioned between saturated aqueous potassium carbonate and chloroform and the chloroform layer was dried (magnesium sulfate), filtered and evaporated to give the title compound as an off-white solid (100 mg), m/z 347 (MH+).

Example 6

(R)-3'-[5-(Thiophen-3-yl)thiophen-2-yl]spiro[1-azabicyclo[2.2.2]octan-3,5'-oxazolidin]-2'-one

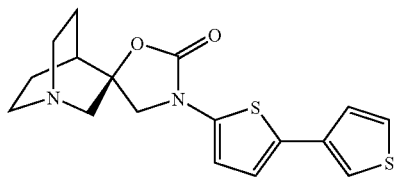

The title compound was prepared by a method analogous to that described in Example 2 from (R)-3'-(5-bromothiophen-2-yl)spiro[1-azabicyclo[2.2.2]octan-3,5'-oxazolidin]-2'-one and thiophene-3-boronic acid. The title compound (118 mg) was obtained as a pale solid, m/z 347 (MH+).

Example 7

(R)-3'-[5-(Furan-2-yl)thiophen-2-yl]spiro[1-azabicyclo[2.2.2]octan-3,5'-oxazolidin]-2'-one

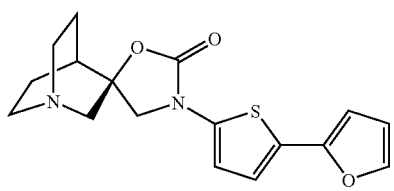

The title compound was prepared by a method analogous to that described in Example 5 from (R)-3'-(5-bromothiophen-2-yl)spiro[1-azabicyclo[2.2.2]octan-3,5'-oxazolidin]-2'-one and 2-(tri-n-butylstannyl)furan. The title compound (52 mg) was obtained as a pale solid, m/z 347 (MH+).

Example 8

(R)-3'-[5-(Furan-3-yl)thiophen-2-yl]spiro[1-azabicyclo[2.2.2]octan-3,5'-oxazolidin]-2'-one

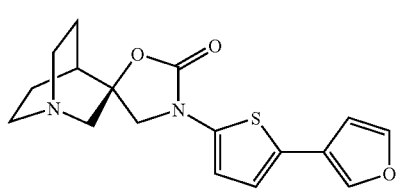

The title compound was prepared by a method analogous to that described in Example 2 from (R)-3'-(5-bromothiophen-2-yl)spiro[1-azabicyclo[2.2.2]octan-3,5'-oxazolidin]-2'-one and furan-3-boronic acid. The title compound (45 mg) was obtained as a pale solid, m/z 347 (MH+).

Example 9

(R)-3'-[5-(Thiazol-2-yl)thiophen-2-yl]spiro[1-azabicyclo[2.2.2]octan-3,5'-oxazolidin]-2'-one

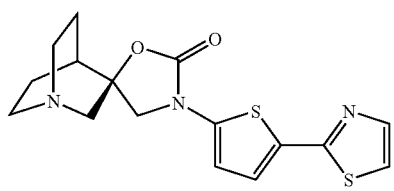

The title compound was prepared by a method analogous to that described in Example 5 from (R)-3'-(5-bromothiophen-2-yl)spiro[1-azabicyclo[2.2.2]octan-3,5'-oxazolidin]-2'-one and 2-(tri-n-butylstannyl)thiazole. The title compound (9 mg) was obtained as a pale solid, m/z 348 (MH+).

Example 10

(R)-3'-[5-(Thiazol-5-yl)thiophen-2-yl]spiro[1-azabicyclo[2.2.2]octan-3,5'-oxazolidin]-2'-one

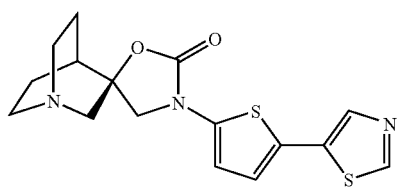

The title compound was prepared by a method analogous to that described in Example 5 from (R)-3'-(5-bromothiophen-2-yl)spiro[1-azabicyclo[2.2.2]octan-3,5'-oxazolidin]-2'-one and 5-(tri-n-butylstannyl)thiazole. The title compound (31 mg) was obtained as a pale solid, m/z 348 (MH+).

Example 11

(R)-3'-[5-(Thiazol-4-yl)thiophen-2-yl]spiro[1-azabicyclo[2.2.2]octan-3,5'-oxazolidin]-2'-one

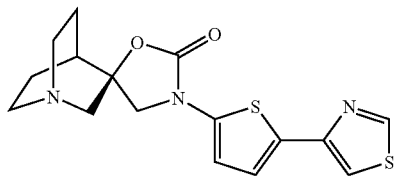

The title compound was prepared by a method analogous to that described in Example 5 from (R)-3'-(5-bromothiophen-2-yl)spiro[1-azabicyclo[2.2.2]octan-3,5'-oxazolidin]-2'-one and 4-(tri-n-butylstannyl)thiazole. The title compound (27 mg) was obtained as a pale solid, m/z 348 (MH+).

Example 12

(R)-3'-[4-(4-Pyridyl)thiophen-2-yl]spiro[1-azabicyclo[2.2.2]octan-3,5'-oxazolidin]-2'-one

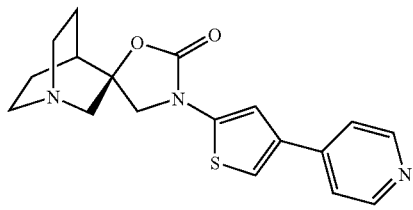

The title compound was prepared by a method analogous to that described in Example 1 from (R)-3'-(4-bromothiophen-2-yl)spiro[1-azabicyclo[2.2.2]octan-3,5'-oxazolidin]-2'-one and pyridine-4-boronic acid. The solid obtained after flash chromatography was further purified by reverse phase HPLC on a Phenomenex® Polar RP column using a gradient of 5-45% acetonitrile/water (each solvent containing 0.1% trifluoroacetic acid as a buffer) as the eluant. The residue was partitioned between saturated aqueous potassium carbonate and chloroform and the chloroform layer was dried (magnesium sulfate), filtered and evaporated to give the title compound as a pale solid (74 mg), m/z 342 (MH+).

Example 13

(R)-3'-[4-(3-Pyridyl)thiophen-2-yl]spiro[1-azabicyclo[2.2.2]octan-3,5'-oxazolidin]-2'-one

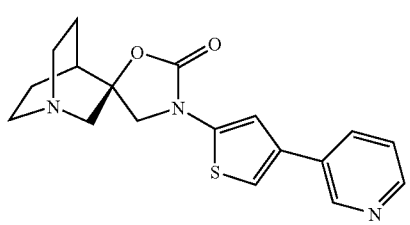

The title compound was prepared by a method analogous to that described in Example 12 from (R)-3'-(4-bromothiophen-2-yl)spiro[1-azabicyclo[2.2.2]octan-3,5'-oxazolidin]-2'-one and pyridine-3-boronic acid. The title compound (73 mg) was obtained as a pale solid, m/z 342 (MH+).

Example 14

(R)-3'-[4-(2-Pyridyl)thiophen-2-yl]spiro[1-azabicyclo[2.2.2]octan-3,5'-oxazolidin]-2'-one

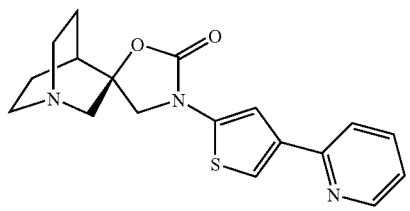

The title compound was prepared by a method analogous to that described in Example 5 from (R)-3'-(4-bromothiophen-2-yl)spiro[1-azabicyclo[2.2.2]octan-3,5'-oxazolidin]-2'-one and 2-(tri-n-butylstannyl)pyridine. The solid obtained from flash chromatography was further purified by reverse phase HPLC on a Polar reverse phase column using a gradient of 5-45% acetonitrile/water (each solvent containing 0.1% trifluoroacetic acid as a buffer) as the eluant. The product-containing fractions were evaporated. The residue was partitioned between saturated aqueous potassium carbonate and chloroform and the chloroform layer was dried (magnesium sulfate), filtered and evaporated to give the title compound as a pale solid, m/z 342 (MH+).

Example 15

(R)-3'-[2-(4-Pyridyl)thiophen-4-yl]spiro[1-azabicyclo[2.2.2]octan-3,5'-oxazolidin]-2'-one

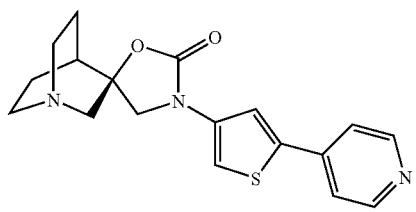

(a) 4-Bromo-2-(4-pyridyl)thiophene

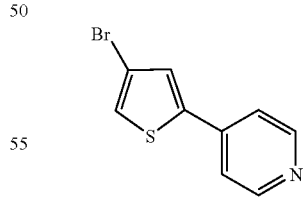

2,4-Dibromothiophene (2.97 g, 12.28 mmol), pyridine-4-boronic acid (1.50 g, 12.28 mmol), potassium carbonate (5.52 g, 39.91 mmol) and tetrakis(triphenylphosphine)palladium (0) (426 mg, 0.38 mmol) were refluxed in ethanol/1,2-dimethoxyethane (1:4 v/v; 100 mL) at 100° C. for 7 hours. The solution was allowed to cool, and then filtered and evaporated. The residue was purified by flash chromatography using a gradient of ethyl acetate in hexane to give a yellow solid as the sub-title compound (1.52 g), m/z 240, 242 (MH+).

(b) (R)-3'-(2-(4-Pyridyl)thiophen-4-yl)spiro[1-azabi-cyclo[2.2.2]octan-3,5'-oxazolidin]-2'-one The title compound was prepared by a method analogous to that described in Preparation 3 from (S)-spiro[1-azabicyclo [2.2.2]octan-3,5'-oxazolidin]-2'-one and 4-bromo-2-(4-pyridyl)thiophene using 2 equivalents of copper (I) iodide. The title compound (1.70 g) was obtained as a pale-yellow solid, m/z 342 (MH$^+$).

Example 16

(R)-3'-(2-(3-Pyridyl)thiophen-4-yl)spiro[1-azabicyclo[2.2.2]octan-3,5'-oxazolidin]-2'-one

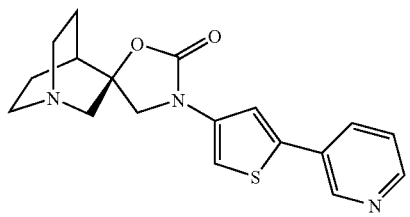

(a) 4-Bromo-2-(3-pyridyl)thiophene

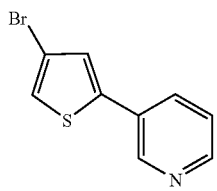

The title compound was prepared by a method analogous to that described in Example 15 for the preparation of 4-bromo-2-(4-pyridyl)thiophene from 2,4-dibromothiophene and pyridine-3-boronic acid. The sub-title compound (2.30 g) was obtained as a pale solid, m/z 240, 242 (MH$^+$).

(b) (R)-3'-[2-(3-Pyridyl)thiophen-4-yl]spiro[1-azabi-cyclo[2.2.2]octan-3,5'-oxazolidin]-2'-one The title compound was prepared by a method analogous to that described in Preparation 3 from (S)-spiro[1-azabicyclo [2.2.2]octan-3,5'-oxazolidin]-2'-one and 4-bromo-2-(3-pyridyl)thiophene. The title compound (800 mg) was obtained as a pale-yellow solid, m/z 342 (MH$^+$).

Example 17

(R)-3'-[2-(2-Pyridyl)thiophen-4-yl]spiro[1-azabicyclo[2.2.2]octan-3,5'-oxazolidin]-2'-one

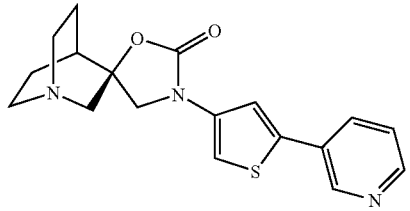

(a) 4-Bromo-2-(2-pyridyl)thiophene

2,4-Dibromothiophene (695 mg, 2.87 mmol), 2-(tri-n-butylstannyl)pyridine (830 mg, 1.92 mmol), and tetrakis(triphenylphosphine)palladium (0) (220 mg, 0.19 mmol) were refluxed in 3 mL of toluene at 120° C. overnight. After filtrated out of solid residue, the reaction mixture was purified by flash chromatography using a gradient of ethyl acetate in hexane to give a beige solid as the title compound (340 mg), m/z 240, 242 (MH$^+$).

(b) (R)-3'-[2-(2-Pyridyl)thiophen-4-yl]spiro[1-azabi-cyclo[2.2.2]octan-3,5'-oxazolidin]-2'-one The title compound was prepared by a method analogous to that described in Preparation 3 from (S)-spiro[1-azabicyclo [2.2.2]octan-3,5'-oxazolidin]-2'-one and 4-bromo-2-(2-pyridyl)thiophene. The title compound (140 mg) was obtained as a pale-yellow solid, m/z 342 (MH$^+$).

Example 18

(R)-3'-(5-Phenylfuran-2-yl)spiro[1-azabicyclo[2.2.2] octan-3,5'-oxazolidin]-2'-one

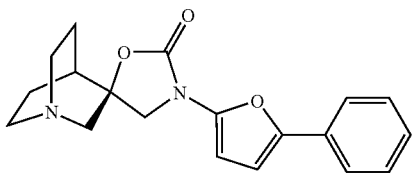

The title compound was prepared by a method analogous to that described in Example 12 from (R)-3'-(5-bromofuran-2-yl)spiro[1-azabicyclo[2.2.2]octan-3,5'-oxazolidin]-2'-one and phenylboronic acid. The title compound (49 mg) was obtained as a pale-yellow solid, m/z 325 (MH$^+$).

Example 19

(R)-3'-[5-(4-Pyridyl)furan-2-yl]spiro[1-azabicyclo [2.2.2]octan-3,5'-oxazolidin]-2'-one

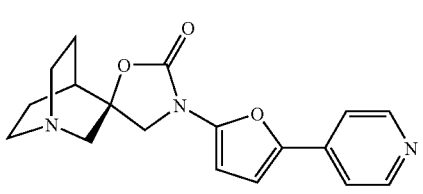

The title compound was prepared by a method analogous to that described in Example 12 from (R)-3'-(5-bromofuran-2-yl)spiro[1-azabicyclo[2.2.2]octan-3,5'-oxazolidin]-2'-one and pyridine-4-boronic acid. The title compound (701 mg) was obtained as a pale solid, m/z 326 (MH$^+$).

Example 20

(R)-3'-[5-(3-Pyridyl)furan-2-yl]spiro[1-azabicyclo [2.2.2]octan-3,5'-oxazolidin]-2'-one

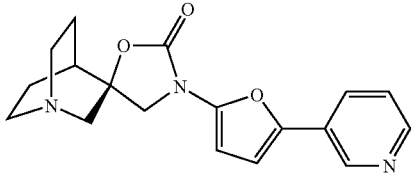

The title compound was prepared by a method analogous to that described in Example 12 from (R)-3'-(5-bromofuran-2-yl)spiro[1-azabicyclo[2.2.2]octan-3,5'-oxazolidin]-2'-one and pyridine-3-boronic acid. The title compound (206 mg) was obtained as a pale solid, m/z 326 (MH$^+$).

Example 21

(R)-3'-[5-(2-Pyridyl)furan-2-yl]spiro[1-azabicyclo [2.2.2]octan-3,5'-oxazolidin]-2'-one

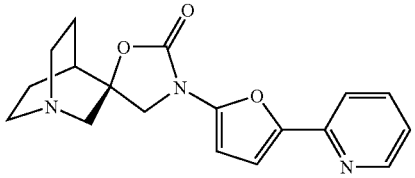

The title compound was prepared by a method analogous to that described in Example 14 from (R)-3'-(5-bromofuran-2-yl)spiro[1-azabicyclo[2.2.2]octan-3,5'-oxazolidin]-2'-one and 2-(tri-n-butylstannyl)pyridine. The title compound (356 mg) was obtained as an off-white solid, m/z 326 (MH$^+$).

Example 22

(R)-3'-[5-(Thiazol-2-yl)furan-2-yl]spiro[1-azabicyclo [2.2.2]octan-3,5'-oxazolidin]-2'-one

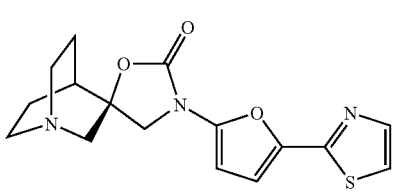

The title compound was prepared by a method analogous to that described in Example 14 from (R)-3'-(5-bromofuran-2-yl)spiro[1-azabicyclo[2.2.2]octan-3,5'-oxazolidin]-2'-one and 2-(tri-n-butylstannyl)thiazole. The title compound (19 mg) was obtained as a pale solid, m/z 332 (MH$^+$).

Example 23

(R)-3'-[5-(Thiazol-5-yl)furan-2-yl]spiro[1-azabicyclo [2.2.2]octan-3,5'-oxazolidin]-2'-one

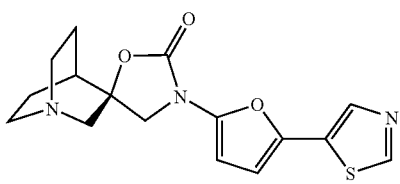

The title compound was prepared by a method analogous to that described in Example 14 from (R)-3'-(5-bromofuran-2-yl)spiro[1-azabicyclo[2.2.2]octan-3,5'-oxazolidin]-2'-one and 5-(tri-n-butylstannyl)thiazole. The title compound (40 mg) was obtained as a pale solid, m/z 332 (MH$^+$).

Example 24

(R)-3'-[5-(Thiazol-4-yl)furan-2-yl]spiro[1-azabicyclo [2.2.2]octan-3,5'-oxazolidin]-2'-one

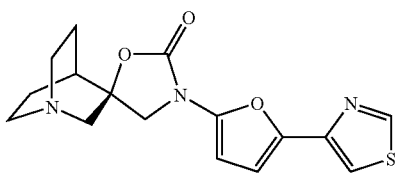

The title compound was prepared by a method analogous to that described in Example 14 from (R)-3'-(5-bromofuran-2-yl)spiro[1-azabicyclo[2.2.2]octan-3,5'-oxazolidin]-2'-one and 4-(tri-n-butylstannyl)thiazole. The title compound (81 mg) was obtained as a pale solid, m/z 332 (MH$^+$).

Example 25

(R)-3'-[4-(4-Pyridyl)furan-2-yl]spiro[1-azabicyclo [2.2.2]octan-3,5'-oxazolidin]-2'-one

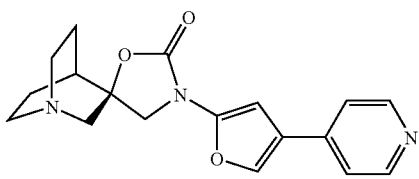

The title compound was prepared by a method analogous to that described in Example 14 from (R)-3'-(4-bromofuran-2-yl)spiro[1-azabicyclo[2.2.2]octan-3,5'-oxazolidin]-2'-one and 4-(tri-n-butylstannyl)pyridine. The title compound (21 mg) was obtained as a pale solid, m/z (MH+).

Example 26

(R)-3'-[4-(3-Pyridyl)furan-2-yl]spiro[1-azabicyclo[2.2.2]octan-3,5'-oxazolidin]-2'-one

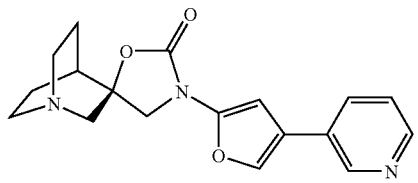

The title compound was prepared by a method analogous to that described in Example 12 from (R)-3'-(4-bromofuran-2-yl)spiro[1-azabicyclo[2.2.2]octan-3,5'-oxazolidin]-2'-one and pyridine-3-boronic acid. The title compound (105 mg) was obtained as a pale solid, m/z 326 (MH+).

Example 27

(R)-3'-[4-(2-Pyridyl)furan-2-yl]spiro[1-azabicyclo[2.2.2]octan-3,5'-oxazolidin]-2'-one

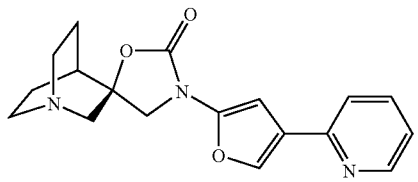

The title compound was prepared by a method analog to that described in Example 14 from (R)-3'-(4-bromofuran-2-yl)spiro[1-azabicyclo[2.2.2]octan-3,5'-oxazolidin]-2'-one and 2-(tri-n-butylstannyl)pyridine. The title compound (20 mg) was obtained as a pale solid, m/z 326 (MH+).

Example 28

(R)-3'-(4-(Pyrazin-2-yl)furan-2-yl)spiro[1-azabicyclo[2.2.2]octan-3,5'-oxazolidin]-2'-one

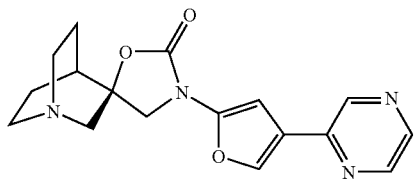

The title compound was prepared by a method analog to that described in Example 14 from (R)-3'-(4-bromofuran-2-yl)spiro[1-azabicyclo[2.2.2]octan-3,5'-oxazolidin]-2'-one and 2-(tri-n-butylstannyl)pyrazine. The title compound (2 mg) was obtained as a pale solid, m/z 327 (MH+).

Example 29

(R)-3'-(Furan-3-yl)spiro[1-azabicyclo[2.2.2]octan-3,5'-oxazolidin]-2'-one

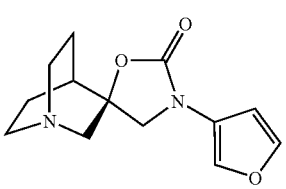

The title compound was prepared by a method analogous to that described in Preparation 3 from (S)-spiro[1-azabicyclo[2.2.2]octan-3,5'-oxazolidin]-2'-one and 3-bromofuran. The title compound (445 mg) was obtained as a pale-yellow solid, m/z 249 (MH+).

Example 30

(R)-3'-[2-(4-Pyridyl)furan-4-yl]spiro[1-azabicyclo[2.2.2]octan-3,5'-oxazolidin]-2'-one

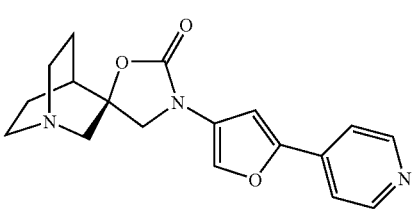

(a) 4-Bromo-2-(4-pyridyl)-furan

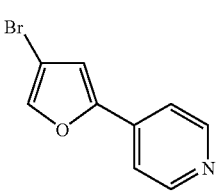

2,4-Dibromo-5-(trimethylsilyl)furan (8.97 g), pyridine-4-boronic acid (1.85 g, 15.1 mmol), potassium carbonate (6.24 g, 45.2 mmol) and tetrakis(triphenylphosphine)palladium (0) (435 mg, 0.38 mmol) were heated under refluxed in ethanol/1,2-dimethoxyethane (1:4 v/v; 100 mL) at 100° C. for 6 h. The solution was allowed to cool, and was then filtered and evaporated. The residue was purified by flash chromatography using a gradient of ethyl acetate in hexane to give the title compounds as a pale brown solid (1.45 g), m/z 224, 226 (MH+).

(b) (R)-3'-[2-(4-Pyridyl)furan-4-yl]spiro[1-azabicyclo[2.2.2]octan-3,5'-oxazolidin]-2'-one The title compound was prepared by a method analogous to that described in Preparation 3 from (S)-spiro[1-azabicyclo[2.2.2]octan-3,5'-oxazolidin]-2'-one and 4-bromo-2-(4-pyridyl)furan using 4 equivalents of copper (I) iodide. The title compound (124 mg) was obtained as a pale yellow solid, m/z 342 (MH⁺).

Example 31

(R)-3'-[2-(3-Pyridyl)furan-4-yl]spiro[1-azabicyclo[2.2.2]octan-3,5'-oxazolidin]-2'-one

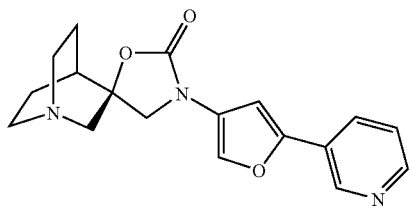

(a) 4-Bromo-2-(3-pyridyl)furan

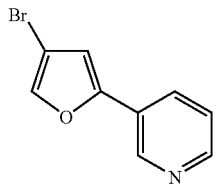

The sub-title compound was prepared by a method analogous to that described for the preparation of 4-bromo-2-(4-pyridyl)-furan from 2,4-dibromo-5-(trimethylsilyl)furan and pyridine-3-boronic acid. The sub-title compound (725 mg) was obtained as a beige solid, m/z 224,226 (MH⁺).

(b) (R)-3'-[2-(3-Pyridyl)furan-4-yl]spiro[1-azabicyclo[2.2.2]octan-3,5'-oxazolidin]-2'-one The title compound was prepared by a method analog to that described in Preparation 3 from (S)-spiro[1-azabicyclo[2.2.2]octan-3,5'-oxazolidin]-2'-one and 3-bromo-5-(3-pyridyl)-furan with 3 equivalents of copper (I) iodide. The title compound (119 mg) was obtained as a pale yellow solid, m/z 342 (MH⁺).

Example 32

(R)-3'-[2-(2-Pyridyl)furan-4-yl]spiro[1-azabicyclo[2.2.2]octan-3,5'-oxazolidin]-2'-one

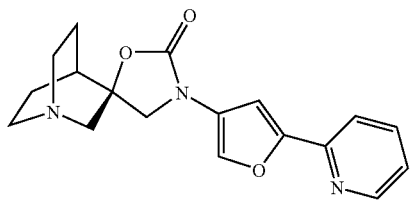

(a) 3-Bromo-5-(2-pyridyl)-3-(trimethylsilyl)furan

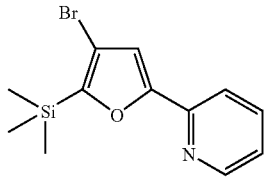

The title compound was prepared by a method analog to that described for the preparation of 4-bromo-2-(2-pyridyl)thiophene from 3,5-dibromo-2-(trimethylsilyl)furan and 2-(tri-n-butylstannyl)pyridine. The title compound (4.96 g) was obtained as a pale brown solid, m/z 296, 298 (MH⁺).

(b) 4-Bromo-2-(2-pyridyl)-furan

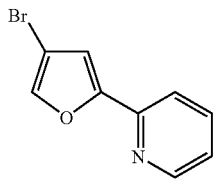

Tetra-n-butylammonium fluoride (1M in tetrahydrofuran, 25.1 mL, 25.11 mmol) was added to a solution of 3-bromo-5-(2-pyridyl)-3-(trimethylsilyl)furan (4.96 g, 16.74 mmol) in tetrahydrofuran (50 mL). The reaction mixture was heated at 70° C. (bath temperature) for six hours. The reaction mixture was evaporated, and the residue was purified by flash chromatography using hexane as the eluant to give the sub-title compound as a pale brown solid (3.02 g), m/z 224, 226 (MH⁺).

(c) (R)-3'-[2-(2-Pyridyl)furan-4-yl]spiro[1-azabicyclo[2.2.2]octan-3,5'-oxazolidin]-2'-one The title compound was prepared by a method analogous to that described in Preparation 3 from (S)-spiro[1-azabicyclo[2.2.2]octan-3,5'-oxazolidin]-2'-one and 3-bromo-5-(2-pyridyl)-furan with 2 equivalents of copper (I) iodide. The title compound (90 mg) was obtained as a pale yellow solid, m/z 342 (MH⁺).

Example 33

3'-[5-(4-Pyridyl)thiazol-2-yl]spiro[1-azabicyclo[2.2.2]octan-3,5'-oxazolidin]-2'-one

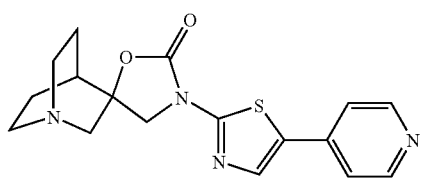

The title compound was prepared by a method analogous to that described in Example 14 from 3'-(5-bromothiazol-2-yl)

spiro[1-azabicyclo[2.2.2]octan-3,5'-oxazolidin]-2'-one and 4-(tri-n-butylstannyl)pyridine. The title compound (52 mg) was obtained as a pale solid, m/z 343 (MH⁺).

Example 34

3'-[5-(3-Pyridyl)thiazol-2-yl]spiro[1-azabicyclo [2.2.2]octan-3,5'-oxazolidin]-2'-one

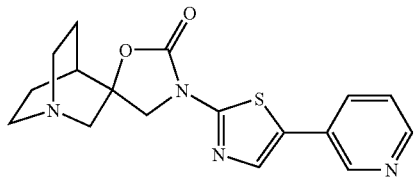

The title compound was prepared by a method analogous to that described in Example 14 from 3'-(5-bromothiazol-2-yl) spiro[1-azabicyclo[2.2.2]octan-3,5'-oxazolidin]-2'-one and 3-(tri-n-butylstannyl)pyridine. The title compound (87 mg) was obtained as a pale solid, m/z 343 (MH⁺).

Example 35

3'-[5-(2-Pyridyl)thiazol-2-yl]spiro[1-azabicyclo [2.2.2]octan-3,5'-oxazolidin]-2'-one

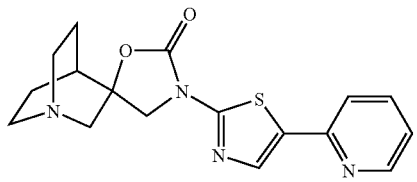

The title compound was prepared by a method analogous to that described in Example 14 from 3'-(5-bromothiazol-2-yl) spiro[1-azabicyclo[2.2.2]octan-3,5'-oxazolidin]-2'-one and 2-(tri-n-butylstannyl)pyridine. The title compound (35 mg) was obtained as a pale solid, m/z 343 (MH⁺).

Examples 36 and 37

(R)-3'-[5-(2-Pyridyl)thiazol-2-yl]spiro[1-azabicyclo [2.2.2]octan-3,5'-oxazolidin]-2'-one (Example 36) and (S)-3'-[5-(2-Pyridyl)thiazol-2-yl)spiro[1-azabicyclo[2.2.2]octan-3,5'-oxazolidin]-2'-one (Example 37)

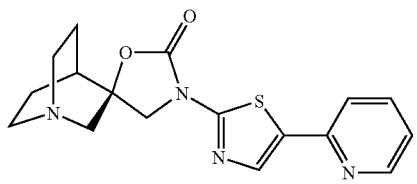

-continued

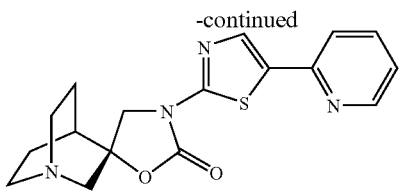

Racemic 3'-[5-(2-pyridyl)thiazol-2-yl]spiro[1-azabicyclo [2.2.2]octan-3,5'-oxazolidin]-2'-one (Example 35) was separated into its enantiomers by chiral supercritical fluid chromatography performed on a Chiral Pak AS-H Column using 1:1 isopropanol and supercritical carbon dioxide containing 0.5% dimethyl ethyl amine as the eluant.to give the title compounds as colourless solids each with m/z 343 (MH⁺).

Example 38

(R)-3'-[4-(4-Pyridyl)thiazol-2-yl]spiro[1-azabicyclo [2.2.2]octan-3,5'-oxazolidin]-2'-one

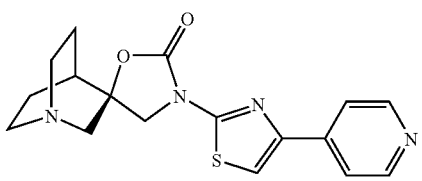

(a) (R)-3'-(4-Bromothiazol-2-yl)spiro[1-azabicyclo [2.2.2]octan-3,5'-oxazolidin]-2'-one

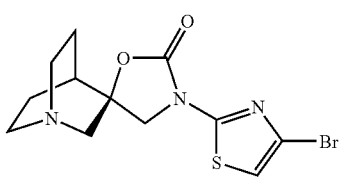

Sodium hydride (265 mg, 6.59 mmol) was added to a solution of (S)-spiro[1-azabicyclo[2.2.2]octan-3,5'-oxazolidin]-2'-one (1.00 g, 5.49 mmol) which was stirred in N,N-dimethyl formamide (15 mL) at room temperature. The reaction mixture then heated to 50° C. for 30 min. 2,4-Dibromothiazole (2.70 g, 10.98 mmol) was added into the reaction mixture and stirring at 50° C. was continued overnight. The mixture was allowed to cool, then quenched with saturated ammonium diluted with a large amount of chloroform. The organic layer was washed with saturated aqueous potassium carbonate and was then dried (magnesium sulfate) and filtered, and the solvent was evaporated. The residue was purified by flash chromatography using a gradient of ammoniated methanol in chloroform to give a solid (369 mg) which was a 1:1 mixture of (R)-3'-(4-bromothiazol-2-yl)spiro[1-azabicyclo[2.2.2]octan-3,5'-oxazolidin]-2'-one, m/z 344, 346 (MH⁺) and (R)-3'-(4,5-dibromothiazol-2-yl)spiro[1-azabicyclo[2.2.2]octan-3,5'-oxazolidin]-2'-one, m/z 422, 424,426 (MH⁺).

(b) (R)-3'-[4-(4-Pyridyl)thiazol-2-yl]spiro[1-azabicyclo[2.2.2]octan-3,5'-oxazolidin]-2'-one The title compound was prepared by a method analogous to that described in Example 14 from the reaction of the mixture of (R)-3'-(4-bromothiazol-2-yl)spiro[1-azabicyclo[2.2.2]octan-3,5'-oxazolidin]-2'-one and (R)-3'-(4,5-dibromothiazol-2-yl)spiro[1-azabicyclo[2.2.2]octan-3,5'-oxazolidin]-2'-one with 4-(tri-n-butylstannyl)pyridine. Separation by reverse phase HPLC separation followed by conversion to the free base as described in Example 14 to give the title compound, m/z 343 (MH$^+$); and (R)-3'-[4,5-di(4-pyridyl)thiazol-2-yl] spiro[1-azabicyclo[2.2.2]octan-3,5'-oxazolidin]-2'-one, m/z 420 (MH$^+$).

Example 39

(R)-3'-[4-(3-Pyridyl)thiazol-2-yl]spiro[1-azabicyclo[2.2.2]octan-3,5'-oxazolidin]-2'-one

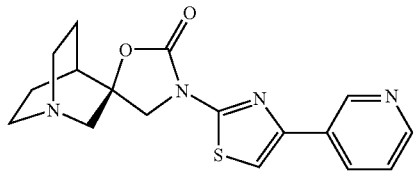

The title compound was prepared by a method analogous to that described in Example 38 using 3-(tri-n-butylstannyl)pyridine. After reverse phase HPLC and conversion to the free base, the title compound, m/z 343 (MH$^+$), and (R)-3'-[4,5-di(3-pyridyl)thiazol-2-yl]spiro[1-azabicyclo[2.2.2]octan-3,5'-oxazolidin]-2'-one (61 mg), m/z 420 (MH$^+$), were obtained as solids.

Example 40

(R)-3'-[4-(2-Pyridyl)thiazol-2-yl]spiro[1-azabicyclo[2.2.2]octan-3,5'-oxazolidin]-2'-one

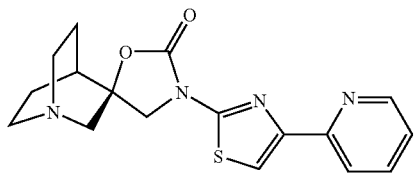

The title compound was prepared by a method analogous to that described in Example 38 using 2-(tri-n-butylstannyl)pyridine. After reverse phase HPLC and conversion to the free base, the title compound, m/z 343 (MH$^+$) and (R)-3'-(4,5-di(2-pyridyl)thiazol-2-yl)spiro[1-azabicyclo[2.2.2]octan-3,5'-oxazolidin]-2'-one, m/e 420 (MH$^+$).

Example 41

(R)-3'-[5-(4-Pyridyl)-1,3,4-thiadiazol-2-yl]spiro[1-azabicyclo[2.2.2]octan-3,5'-oxazolidin]-2'-one

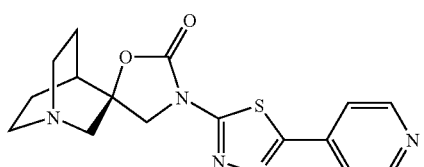

(a) 2-Bromo-5-(4-pyridyl)-1,3,4-thiadiazole

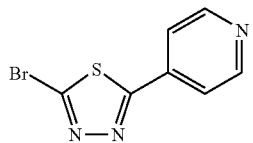

2-Amino-5-(4-pyridyl)-1,3,4-thiadiazole (2.0 g, 11.2 mmol) was suspended in 48% aqueous hydrobromic acid (5.6 mL) and stirred at 0° C. Bromine (5.06 mL, 98.8 mmol) was added dropwise into the mixture at 0° C. Water (15 mL) was added slowly followed by a solution of sodium nitrite (1.97 g, 28.6 mmol) in water (2.8 mL). Stirring at 0° C. was continued for another 30 minutes. Sodium hydroxide (10.0 g) in water (10 mL) was added slowly into the reaction mixture while the temperature was maintained below 20° C. The reaction mixture was then extracted with chloroform then the chloroform solution was washed with water, dried (magnesium sulfate), filtered, and the solvent was evaporated. The residue was purified by flash chromatography using a gradient of ethyl acetate in hexane to give the title compound as a brown solid (1.28 g), m/z 242, 244 (MH$^+$).

(b) (R)-3'-[5-(4-Pyridyl)-1,3,4-thiadiazol-2-yl]spiro[1-azabicyclo[2.2.2]octan-3,5'-oxazolidin]-2'-one The compound was prepared by a method analogous to that described in Preparation 3 from (S)-spiro[1-azabicyclo[2.2.2]octan-3,5'-oxazolidin]-2'-one and 2-bromo-5-(4-pyridyl)-1,3,4-thiadiazole using 5 equivalents of copper (I) iodide. The title compound was obtained as a beige solid, m/z 344 (MH$^+$).

Example 42

(R)-3'-(5-Phenyl-1,3,4-thiadiazol-2-yl)spiro[1-azabicyclo[2.2.2]octan-3,5'-oxazolidin]-2'-one

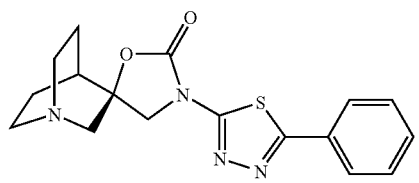

(a) 2-Bromo-5-phenyl-1,3,4-thiadiazole

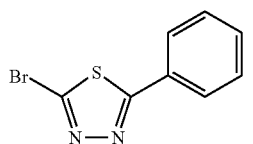

The compound was prepared by a method analogous to that described in Example 41(a) from 2-amino-5-phenyl-1,3,4-thiadiazole. The sub-title compound was obtained as a colourless solid, m/z 241, 243 (MH$^+$).

(b) (R)-3'-(5-Phenyl-1,3,4-thiadiazol-2-yl)spiro[1-azabicyclo[2.2.2]octan-3,5'-oxazolidin]-2'-one The compound was prepared by a method analogous to that described in Preparation 3 from (S)-spiro[1-azabicyclo [2.2.2]octan-3,5'-oxazolidin]-2'-one and 2-bromo-5-phenyl-1,3,4-thiadiazole using 5 equivalents of copper (I) iodide. The title compound (180 mg) was obtained as a yellow solid, m/z 343 (MH$^+$).

Example 43

(R)-3'-[5-(2-Pyrazolyl)thiophen-2-yl]spiro[1-azabicyclo[2.2.2]octan-3,5'-oxazolidin]-2'-one

(a) 2-Bromo-5-(2-pyrazolyl)thiophene

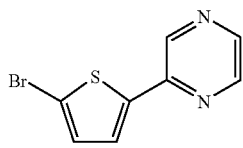

A solution containing 2,5-dibromothiophene (5.0 mL, 10.3 g, 44.4 mmol), 2-(tri-n-butylstannyl)pyrazole (4.09 g, 11.0 mmol), tetrakis(triphenylphosphine)palladium (0) (0.67 g, 0.58 mmol) in toluene (50 mL) was heated under reflux under an argon atmosphere for 6 h. The solution was evaporated and the residue was subjected to flash chromatography on silica using a gradient of 0-25% ethyl acetate/hexane as the eluant. Evaporation of the product-containing fractions gave the sub-title compound (771 mg) as a solid, m/z 241, 243 (MH$^+$).

(b) (R)-3'-[5-(2-Pyrazolyl)thiophen-2-yl]spiro[1-azabicyclo[2.2.2]octan-3,5'-oxazolidin]-2'-one The compound was prepared by a method analog to that described in Preparation 3 from (S)-spiro[1-azabicyclo [2.2.2]octan-3,5'-oxazolidin]-2'-one and 2-bromo-5-(2-pyrazolyl)thiophene using 3.6 equivalents of copper (I) iodide. The title compound was obtained as a pale solid, m/z 343 (MH$^+$).

The present invention includes by representation, but not by limitation, the following compounds and pharmaceutically-acceptable salts thereof which may be prepared by those skilled in the art using processes and methods analogous to those described herein:
(R)-3'-(5-phenylthiophen-2-yl)spiro[1-azabicyclo[2.2.2]octan-3,5'-oxazolidin]-2'-one;
(R)-3'-[5-(4-pyridyl)thiophen-2-yl]spiro[1-azabicyclo [2.2.2]octan-3,5'-oxazolidin]-2'-one;
(R)-3'-[5-(3-pyridyl)thiophen-2-yl]spiro[1-azabicyclo [2.2.2]octan-3,5'-oxazolidin]-2'-one;
(R)-3'-[5-(2-pyridyl)thiophen-2-yl]spiro[1-azabicyclo [2.2.2]octan-3,5'-oxazolidin]-2'-one;
(R)-3'-[5-(thiophen-2-yl)thiophen-2-yl]spiro[1-azabicyclo [2.2.2]octan-3,5'-oxazolidin]-2'-one;
(R)-3'-[5-(thiophen-3-yl)thiophen-2-yl]spiro[1-azabicyclo [2.2.2]octan-3,5'-oxazolidin]-2'-one;
(R)-3'-[5-(furan-2-yl)thiophen-2-yl]spiro[1-azabicyclo [2.2.2]octan-3,5'-oxazolidin]-2'-one;
(R)-3'-[5-(furan-3-yl)thiophen-2-yl]spiro[1-azabicyclo [2.2.2]octan-3,5'-oxazolidin]-2'-one;
(R)-3'-[5-(thiazol-2-yl)thiophen-2-yl]spiro[1-azabicyclo [2.2.2]octan-3,5'-oxazolidin]-2'-one;
(R)-3'-[5-(thiazol-4-yl)thiophen-2-yl]spiro[1-azabicyclo [2.2.2]octan-3,5'-oxazolidin]-2'-one;
(R)-3'-[5-(thiazol-5-yl)thiophen-2-yl]spiro[1-azabicyclo [2.2.2]octan-3,5'-oxazolidin]-2'-one;
(R)-3'-(4-phenylthiophen-2-yl)spiro[1-azabicyclo[2.2.2]octan-3,5'-oxazolidin]-2'-one;
(R)-3'-[4-(4-pyridyl)thiophen-2-yl]spiro[1-azabicyclo [2.2.2]octan-3,5'-oxazolidin]-2'-one;
(R)-3'-[4-(3-pyridyl)thiophen-2-yl]spiro[1-azabicyclo [2.2.2]octan-3,5'-oxazolidin]-2'-one;
(R)-3'-[4-(2-pyridyl)thiophen-2-yl]spiro[1-azabicyclo [2.2.2]octan-3,5'-oxazolidin]-2'-one;
(R)-3'-[4-(thiophen-2-yl)thiophen-2-yl]spiro[1-azabicyclo [2.2.2]octan-3,5'-oxazolidin]-2'-one;
(R)-3'-[4-(thiophen-3-yl)thiophen-2-yl]spiro[1-azabicyclo [2.2.2]octan-3,5'-oxazolidin]-2'-one;
(R)-3'-[4-(furan-2-yl)thiophen-2-yl]spiro[1-azabicyclo [2.2.2]octan-3,5'-oxazolidin]-2'-one;
(R)-3'-[4-(furan-3-yl)thiophen-2-yl]spiro[1-azabicyclo [2.2.2]octan-3,5'-oxazolidin]-2'-one;
(R)-3'-[4-(thiazol-2-yl)thiophen-2-yl]spiro[1-azabicyclo [2.2.2]octan-3,5'-oxazolidin]-2'-one;
(R)-3'-[4-(thiazol-4-yl)thiophen-2-yl]spiro[1-azabicyclo [2.2.2]octan-3,5'-oxazolidin]-2'-one;
(R)-3'-[4-(thiazol-5-yl)thiophen-2-yl]spiro[1-azabicyclo [2.2.2]octan-3,5'-oxazolidin]-2'-one;
(R)-3'-(2-phenylthiophen-4-yl)spiro[1-azabicyclo[2.2.2]octan-3,5'-oxazolidin]-2'-one;
(R)-3'-[2-(4-pyridyl)thiophen-4-yl]spiro[1-azabicyclo [2.2.2]octan-3,5'-oxazolidin]-2'-one;
(R)-3'-[2-(3-pyridyl)thiophen-4-yl]spiro[1-azabicyclo [2.2.2]octan-3,5'-oxazolidin]-2'-one;
(R)-3'-[2-(2-pyridyl)thiophen-4-yl]spiro[1-azabicyclo [2.2.2]octan-3,5'-oxazolidin]-2'-one;
(R)-3'-[2-(thiophen-2-yl)thiophen-4-yl]spiro[1-azabicyclo [2.2.2]octan-3,5'-oxazolidin]-2'-one;
(R)-3'-[2-(thiophen-3-yl)thiophen-4-yl]spiro[1-azabicyclo [2.2.2]octan-3,5'-oxazolidin]-2'-one;
(R)-3'-[2-(furan-2-yl)thiophen-4-yl]spiro[1-azabicyclo [2.2.2]octan-3,5'-oxazolidin]-2'-one;
(R)-3'-[2-(furan-3-yl)thiophen-4-yl]spiro[1-azabicyclo [2.2.2]octan-3,5'-oxazolidin]-2'-one;
(R)-3'-[2-(thiazol-2-yl)thiophen-4-yl]spiro[1-azabicyclo [2.2.2]octan-3,5'-oxazolidin]-2'-one;
(R)-3'-[2-(thiazol-4-yl)thiophen-4-yl]spiro[1-azabicyclo [2.2.2]octan-3,5'-oxazolidin]-2'-one;
(R)-3'-[2-(thiazol-5-yl)thiophen-4-yl]spiro[1-azabicyclo [2.2.2]octan-3,5'-oxazolidin]-2'-one;
(R)-3'-(5-phenylfuran-2-yl)spiro[1-azabicyclo[2.2.2]octan-3,5'-oxazolidin]-2'-one;
(R)-3'-[5-(4-pyridyl)furan-2-yl]spiro[1-azabicyclo[2.2.2]octan-3,5'-oxazolidin]-2'-one;
(R)-3'-[5-(3-pyridyl)furan-2-yl]spiro[1-azabicyclo[2.2.2]octan-3,5'-oxazolidin]-2'-one;

(R)-3'-[5-(2-pyridyl)furan-2-yl]spiro[1-azabicyclo[2.2.2]octan-3,5'-oxazolidin]-2'-one;
(R)-3'-[5-(thiophen-2-yl)furan-2-yl]spiro[1-azabicyclo[2.2.2]octan-3,5'-oxazolidin]-2'-one;
(R)-3'-[5-(thiophen-3-yl)furan-2-yl]spiro[1-azabicyclo[2.2.2]octan-3,5'-oxazolidin]-2'-one;
(R)-3'-[5-(furan-2-yl)furan-2-yl]spiro[1-azabicyclo[2.2.2]octan-3,5'-oxazolidin]-2'-one;
(R)-3'-[5-(furan-3-yl)furan-2-yl]spiro[1-azabicyclo[2.2.2]octan-3,5'-oxazolidin]-2'-one;
(R)-3'-[5-(thiazol-2-yl)furan-2-yl]spiro[1-azabicyclo[2.2.2]octan-3,5'-oxazolidin]-2'-one;
(R)-3'-[5-(thiazol-4-yl)furan-2-yl]spiro[1-azabicyclo[2.2.2]octan-3,5'-oxazolidin]-2'-one;
(R)-3'-[5-(thiazol-5-yl)furan-2-yl]spiro[1-azabicyclo[2.2.2]octan-3,5'-oxazolidin]-2'-one;
(R)-3'-(4-phenylfuran-2-yl)spiro[1-azabicyclo[2.2.2]octan-3,5'-oxazolidin]-2'-one;
(R)-3'-[4-(4-pyridyl)furan-2-yl]spiro[1-azabicyclo[2.2.2]octan-3,5'-oxazolidin]-2'-one;
(R)-3'-[4-(3-pyridyl)furan-2-yl]spiro[1-azabicyclo[2.2.2]octan-3,5'-oxazolidin]-2'-one;
(R)-3'-[4-(2-pyridyl)furan-2-yl]spiro[1-azabicyclo[2.2.2]octan-3,5'-oxazolidin]-2'-one;
(R)-3'-[4-(thiophen-2-yl)furan-2-yl]spiro[1-azabicyclo[2.2.2]octan-3,5'-oxazolidin]-2'-one;
(R)-3'-[4-(thiophen-3-yl)furan-2-yl]spiro[1-azabicyclo[2.2.2]octan-3,5'-oxazolidin]-2'-one;
(R)-3'-[4-(furan-2-yl)furan-2-yl]spiro[1-azabicyclo[2.2.2]octan-3,5'-oxazolidin]-2'-one;
(R)-3'-[4-(furan-3-yl)furan-2-yl]spiro[1-azabicyclo[2.2.2]octan-3,5'-oxazolidin]-2'-one;
(R)-3'-[4-(thiazol-2-yl)furan-2-yl]spiro[1-azabicyclo[2.2.2]octan-3,5'-oxazolidin]-2'-one;
(R)-3'-[4-(thiazol-4-yl)furan-2-yl]spiro[1-azabicyclo[2.2.2]octan-3,5'-oxazolidin]-2'-one;
(R)-3'-[4-(thiazol-5-yl)furan-2-yl]spiro[1-azabicyclo[2.2.2]octan-3,5'-oxazolidin]-2'-one;
(R)-3'-(2-phenylfuran-4-yl)spiro[1-azabicyclo[2.2.2]octan-3,5'-oxazolidin]-2'-one;
(R)-3'-[2-(4-pyridyl)furan-4-yl]spiro[1-azabicyclo[2.2.2]octan-3,5'-oxazolidin]-2'-one;
(R)-3'-[2-(3-pyridyl)furan-4-yl]spiro[1-azabicyclo[2.2.2]octan-3,5'-oxazolidin]-2'-one;
(R)-3'-[2-(2-pyridyl)furan-4-yl]spiro[1-azabicyclo[2.2.2]octan-3,5'-oxazolidin]-2'-one;
(R)-3'-[2-(thiophen-2-yl)furan-4-yl]spiro[1-azabicyclo[2.2.2]octan-3,5'-oxazolidin]-2'-one;
(R)-3'-[2-(thiophen-3-yl)furan-4-yl]spiro[1-azabicyclo[2.2.2]octan-3,5'-oxazolidin]-2'-one;
(R)-3'-[2-(furan-2-yl)furan-4-yl]spiro[1-azabicyclo[2.2.2]octan-3,5'-oxazolidin]-2'-one;
(R)-3'-[2-(furan-3-yl)furan-4-yl]spiro[1-azabicyclo[2.2.2]octan-3,5'-oxazolidin]-2'-one;
(R)-3'-[2-(thiazol-2-yl)furan-4-yl]spiro[1-azabicyclo[2.2.2]octan-3,5'-oxazolidin]-2'-one;
(R)-3'-[2-(thiazol-4-yl)furan-4-yl]spiro[1-azabicyclo[2.2.2]octan-3,5'-oxazolidin]-2'-one;
(R)-3'-[2-(thiazol-5-yl)furan-4-yl]spiro[1-azabicyclo[2.2.2]octan-3,5'-oxazolidin]-2'-one;
3'-[5-(4-pyridyl)-thiazol-2-yl]spiro[1-azabicyclo[2.2.2]octan-3,5'-oxazolidin]-2'-one;
3'-[5-(3-pyridyl)-thiazol-2-yl]spiro[1-azabicyclo[2.2.2]octan-3,5'-oxazolidin]-2'-one;
3'-[5-(2-pyridyl)-thiazol-2-yl]spiro[1-azabicyclo[2.2.2]octan-3,5'-oxazolidin]-2'-one;
(R)-3'-[5-(2-pyridyl)-thiazol-2-yl]spiro[1-azabicyclo[2.2.2]octan-3,5'-oxazolidin]-2'-one;
(S)-3'-[5-(2-pyridyl)-thiazol-2-yl]spiro[1-azabicyclo[2.2.2]octan-3,5'-oxazolidin]-2'-one;
(R)-3'-[4-(4-pyridyl)-thiazol-2-yl]spiro[1-azabicyclo[2.2.2]octan-3,5'-oxazolidin]-2'-one;
(R)-3'-[4-(3-pyridyl)-thiazol-2-yl]spiro[1-azabicyclo[2.2.2]octan-3,5'-oxazolidin]-2'-one; and
(R)-3'-[4-(2-pyridyl)-thiazol-2-yl]spiro[1-azabicyclo[2.2.2]octan-3,5'-oxazolidin]-2'-one.

The present invention also includes by representation, but not by limitation, the following compounds and pharmaceutically-acceptable salts thereof which may be prepared by those skilled in the art using processes and methods analogous to those described herein:
(R)-3'-{5-[3-(N,N-dimethylcarbamoyl)phenyl]thiophen-2-yl}spiro[1-azabicyclo[2.2.2]octan-3,5'-oxazolidin]-2'-one;
(R)-3'-{5-[3-(N,N-diethylcarbamoyl)phenyl]thiophen-2-yl}spiro[1-azabicyclo[2.2.2]octan-3,5'-oxazolidin]-2'-one;
(R)-3'-{5-[3-(pyrrolidine-1-carbonyl)phenyl]thiophen-2-yl}spiro[1-azabicyclo[2.2.2]octan-3,5'-oxazolidin]-2'-one;
(R)-3'-{5-[3-(piperidine-1-carbonyl)phenyl]thiophen-2-yl}spiro[1-azabicyclo[2.2.2]octan-3,5'-oxazolidin]-2'-one;
(R)-3'-{5-[3-(morpholine-4-carbonyl)phenyl]thiophen-2-yl}spiro[1-azabicyclo[2.2.2]octan-3,5'-oxazolidin]-2'-one;
(R)-3'-[5-(3-aminophenyl)thiophen-2-yl]spiro[1-azabicyclo[2.2.2]octan-3,5'-oxazolidin]-2'-one;
(R)-3'-{5-[3-(N,N-dimethylamino)phenyl]thiophen-2-yl}spiro[1-azabicyclo[2.2.2]octan-3,5'-oxazolidin]-2'-one;
(R)-3'-{5-[3-(propionylamino)phenyl]thiophen-2-yl}spiro[1-azabicyclo[2.2.2]octan-3,5'-oxazolidin]-2'-one;
(R)-3'-{5-[3-(butyrylamino)phenyl]thiophen-2-yl}spiro[1-azabicyclo[2.2.2]octan-3,5'-oxazolidin]-2'-one;
(R)-3'-{5-[3-(benzoylamino)phenyl]thiophen-2-yl}spiro[1-azabicyclo[2.2.2]octan-3,5'-oxazolidin]-2'-one;
(R)-3'-{5-[3-(2-propoxy)phenyl]thiophen-2-yl}spiro[1-azabicyclo[2.2.2]octan-3,5'-oxazolidin]-2'-one;
(R)-3'-[5-(3-trifluoromethoxyphenyl)thiophen-2-yl]spiro[1-azabicyclo[2.2.2]octan-3,5'-oxazolidin]-2'-one;
(R)-3'-[5-(quinolin-2-yl)thiophen-2-yl]spiro[1-azabicyclo[2.2.2]octan-3,5'-oxazolidin]-2'-one;
(R)-3'-[5-(quinolin-3-yl)thiophen-2-yl]spiro[1-azabicyclo[2.2.2]octan-3,5'-oxazolidin]-2'-one;
(R)-3'-[5-(quinolin-4-yl)thiophen-2-yl]spiro[1-azabicyclo[2.2.2]octan-3,5'-oxazolidin]-2'-one;
(R)-3'-[5-(quinolin-5-yl)thiophen-2-yl]spiro[1-azabicyclo[2.2.2]octan-3,5'-oxazolidin]-2'-one;
(R)-3'-[5-(quinolin-6-yl)thiophen-2-yl]spiro[1-azabicyclo[2.2.2]octan-3,5'-oxazolidin]-2'-one;
(R)-3'-[5-(quinolin-7-yl)thiophen-2-yl]spiro[1-azabicyclo[2.2.2]octan-3,5'-oxazolidin]-2'-one;
(R)-3'-[5-(quinolin-8-yl)thiophen-2-yl]spiro[1-azabicyclo[2.2.2]octan-3,5'-oxazolidin]-2'-one;
(R)-3'-[5-(pyrimidin-2-yl)thiophen-2-yl]spiro[1-azabicyclo[2.2.2]octan-3,5'-oxazolidin]-2'-one;
(R)-3'-[5-(pyrimidin-4-yl)thiophen-2-yl]spiro[1-azabicyclo[2.2.2]octan-3,5'-oxazolidin]-2'-one;
(R)-3'-[5-(pyrimidin-5-yl)thiophen-2-yl]spiro[(1-azabicyclo[2.2.2]octan-3,5'-oxazolidin]-2'-one;
(R)-3'-(2-phenylthiazol-4-yl)spiro[1-azabicyclo[2.2.2]octan-3,5'-oxazolidin]-2'-one;

(R)-3'-[2-(2-pyridyl)thiazol-4-yl]spiro[1-azabicyclo[2.2.2]octan-3,5'-oxazolidin]-2'-one;
(R)-3'-[2-(3-pyridyl)thiazol-4-yl]spiro[1-azabicyclo[2.2.2]octan-3,5'-oxazolidin]-2'-one;
(R)-3'-[2-(4-pyridyl)thiazol-4-yl]spiro[1-azabicyclo[2.2.2]octan-3,5'-oxazolidin]-2'-one;
(R)-3'-(2-phenylthiazol-5-yl)spiro[1-azabicyclo[2.2.2]octan-3,5'-oxazolidin]-2'-one;
(R)-3'-[2-(2-pyridyl)thiazol-5-yl]spiro[1-azabicyclo[2.2.2]octan-3,5'-oxazolidin]-2'-one;
(R)-3'-[2-(3-pyridyl)thiazol-5-yl]spiro[1-azabicyclo[2.2.2]octan-3,5'-oxazolidin]-2'-one;
(R)-3'-[2-(4-pyridyl)thiazol-5-yl]spiro[1-azabicyclo[2.2.2]octan-3,5'-oxazolidin]-2'-one;
(R)-3'-[5-(2-pyridyl)-1,3,4-thiadiazol-2-yl]spiro[1-azabicyclo[2.2.2]octan-3,5'-oxazolidin]-2'-one;
(R)-3'-[5-(3-pyridyl)-1,3,4-thiadiazol-2-yl]spiro[1-azabicyclo[2.2.2]octan-3,5'-oxazolidin]-2'-one;
(R)-3'-(5-phenyl-1,3,4-oxadiazol-2-yl)spiro[1-azabicyclo[2.2.2]octan-3,5'-oxazolidin]-2'-one;
(R)-3'-(5-phenyloxazol-2-yl)spiro[1-azabicyclo[2.2.2]octan-3,5'-oxazolidin]-2'-one;
(R)-3'-[5-(2-pyridyl)oxazol-2-yl]spiro[1-azabicyclo[2.2.2]octan-3,5'-oxazolidin]-2'-one;
(R)-3'-[5-(3-pyridyl)thiazol-2-yl]spiro[1-azabicyclo[2.2.2]octan-3,5'-oxazolidin]-2'-one;
(R)-3'-[5-(4-pyridyl)thiazol-2-yl]spiro[1-azabicyclo[2.2.2]octan-3,5'-oxazolidin]-2'-one;
(R)-3'-(4-phenyloxazol-2-yl)spiro[1-azabicyclo[2.2.2]octan-3,5'-oxazolidin]-2'-one;
(R)-3'-[4-(2-pyridyl)oxazol-2-yl]spiro[1-azabicyclo[2.2.2]octan-3,5'-oxazolidin]-2'-one;
(R)-3'-[4-(3-pyridyl)thiazol-2-yl]spiro[1-azabicyclo[2.2.2]octan-3,5'-oxazolidin]-2'-one;
(R)-3'-[4-(4-pyridyl)thiazol-2-yl]spiro[1-azabicyclo[2.2.2]octan-3,5'-oxazolidin]-2'-one;
(R)-3'-(2-phenyloxazol-4-yl)spiro[1-azabicyclo[2.2.2]octan-3,5'-oxazolidin]-2'-one;
(R)-3'-[2-(2-pyridyl)oxazol-4-yl]spiro[1-azabicyclo[2.2.2]octan-3,5'-oxazolidin]-2'-one;
(R)-3'-[2-(3-pyridyl)thiazol-4-yl]spiro[1-azabicyclo[2.2.2]octan-3,5'-oxazolidin]-2'-one;
(R)-3'-[2-(4-pyridyl)thiazol-4-yl]spiro[1-azabicyclo[2.2.2]octan-3,5'-oxazolidin]-2'-one;
(R)-3'-(2-phenyloxazol-5-yl)spiro[1-azabicyclo[2.2.2]octan-3,5'-oxazolidin]-2'-one;
(R)-3'-[2-(2-pyridyl)oxazol-5-yl]spiro[1-azabicyclo[2.2.2]octan-3,5'-oxazolidin]-2'-one;
(R)-3'-[2-(3-pyridyl)thiazol-5-yl]spiro[1-azabicyclo[2.2.2]octan-3,5'-oxazolidin]-2'-one;
(R)-3'-[2-(4-pyridyl)thiazol-5-yl]spiro[1-azabicyclo[2.2.2]octan-3,5'-oxazolidin]-2'-one;
(R)-3'-[5-(2-pyridyl)-1,3,4-oxadiazol-2-yl]spiro[1-azabicyclo[2.2.2]octan-3,5'-oxazolidin]-2'-one;
(R)-3'-[5-(3-pyridyl)-1,3,4-oxadiazol-2-yl]spiro[1-azabicyclo[2.2.2]octan-3,5'-oxazolidin]-2'-one; and
(R)-3'-[5-(4-pyridyl)-1,3,4-oxadiazol-2-yl]spiro[1-azabicyclo[2.2.2]octan-3,5'-oxazolidin]-2'-one;

The present invention further includes by representation, but not by limitation, the following compounds and pharmaceutically-acceptable salts thereof which may be prepared by those skilled in the art using processes and methods analogous to those described herein:

(R)-3'-[5-(2-fluorophenyl)thiophen-2-yl]spiro[1-azabicyclo[2.2.2]octan-3,5'-oxazolidin]-2'-one;
(R)-3'-[5-(3-fluorophenyl)thiophen-2-yl]spiro[1-azabicyclo[2.2.2]octan-3,5'-oxazolidin]-2'-one;
(R)-3'-[5-(4-fluorophenyl)thiophen-2-yl]spiro[1-azabicyclo[2.2.2]octan-3,5'-oxazolidin]-2'-one;
(R)-3'-[5-(2-chlorophenyl)thiophen-2-yl]spiro[1-azabicyclo[2.2.2]octan-3,5'-oxazolidin]-2'-one;
(R)-3'-[5-(3-chlorophenyl)thiophen-2-yl]spiro[1-azabicyclo[2.2.2]octan-3,5'-oxazolidin]-2'-one;
(R)-3'-[5-(4-chlorophenyl)thiophen-2-yl]spiro[1-azabicyclo[2.2.2]octan-3,5'-oxazolidin]-2'-one;
(R)-3'-[5-(3,4-dichlorophenyl)thiophen-2-yl]spiro[1-azabicyclo[2.2.2]octan-3,5'-oxazolidin]-2'-one;
(R)-3'-[5-(3-methylphenyl)thiophen-2-yl]spiro[5-azabicyclo[2.2.2]octan-3,5'-oxazolidin]-2'-one;
(R)-3'-[5-(4-methylphenyl)thiophen-2-yl]spiro[1-azabicyclo[2.2.2]octan-3,5'-oxazolidin]-2'-one;
(R)-3'-[5-(3-methoxyphenyl)thiophen-2-yl]spiro[1-azabicyclo[2.2.2]octan-3,5'-oxazolidin]-2'-one;
(R)-3'-[5-(4-methoxyphenyl)thiophen-2-yl]spiro[1-azabicyclo[2.2.2]octan-3,5'-oxazolidin]-2'-one;
(R)-3'-[5-(3-methoxyphenyl)thiophen-2-yl]spiro[1-azabicyclo[2.2.2]octan-3,5'-oxazolidin]-2'-one;
(R)-3'-[5-(3-trifluoromethylphenyl)thiophen-2-yl]spiro[1-azabicyclo[2.2.2]octan-3,5'-oxazolidin]-2'-one;
(R)-3'-[5-(4-trifluoromethylphenyl)thiophen-2-yl]spiro[1-azabicyclo[2.2.2]octan-3,5'-oxazolidin]-2'-one;
(R)-3'-[5-(3-trifluoromethoxyphenyl)thiophen-2-yl]spiro[1-azabicyclo[2.2.2]octan-3,5'-oxazolidin]-2'-one;
(R)-3'-[5-(4-trifluoromethoxyphenyl)thiophen-2-yl]spiro[1-azabicyclo[2.2.2]octan-3,5'-oxazolidin]-2'-one;
(R)-3'-[5-(naphthalen-2-yl)thiophen-2-yl]spiro[1-azabicyclo[2.2.2]octan-3,5'-oxazolidin]-2'-one;
(R)-3'-[5-(benzofuran-2-yl)thiophen-2-yl]spiro[1-azabicyclo[2.2.2]octan-3,5'-oxazolidin]-2'-one;
(R)-3'-[5-(benzo[b]thiophen-2-yl)thiophen-2-yl]spiro[1-azabicyclo[2.2.2]octan-3,5'-oxazolidin]-2'-one;
(R)-3'-[5-(2-fluoropyridin-3-yl)thiophen-2-yl]spiro[1-azabicyclo[2.2.2]octan-3,5'-oxazolidin]-2'-one;
(R)-3'-[5-(2-chloropyridin-3-yl)thiophen-2-yl]spiro[1-azabicyclo[2.2.2]octan-3,5'-oxazolidin]-2'-one;
(R)-3'-[5-(2-methoxypyridin-3-yl)thiophen-2-yl]spiro[1-azabicyclo[2.2.2]octan-3,5'-oxazolidin]-2'-one;
(R)-3'-[5-(2-aminopyridin-3-yl)thiophen-2-yl]spiro[1-azabicyclo[2.2.2]octan-3,5'-oxazolidin]-2'-one;
(R)-3'-{5-[2-(N,N-dimethylamino)pyridin-3-yl]thiophen-2-yl}spiro[1-azabicyclo[2.2.2]octan-3,5'-oxazolidin]-2'-one;
(R)-3'-[5-(5-chloropyridin-3-yl)thiophen-2-yl]spiro[1-azabicyclo[2.2.2]octan-3,5'-oxazolidin]-2'-one;
(R)-3'-[5-(5-methoxypyridin-3-yl)thiophen-2-yl]spiro[1-azabicyclo[2.2.2]octan-3,5'-oxazolidin]-2'-one;
(R)-3'-[5-(5-aminopyridin-3-yl)thiophen-2-yl]spiro[1-azabicyclo[2.2.2]octan-3,5'-oxazolidin]-2'-one; and
(R)-3'-{5-[5-(N,N-dimethylamino)pyridin-3-yl]thiophen-2-yl}spiro[1-azabicyclo[2.2.2]octan-3,5'-oxazolidin]-2'-one.

Pharmacology

The pharmacological activity of compounds of the invention may be measured using the tests set out below:

Test A—Assay for Affinity at α7 nAChR Subtype

[$^{125}$I]-α-Bungarotoxin (BTX) binding to rat hippocampal membranes. Rat hippocampi were homogenized in 20 volumes of cold homogenization buffer (HB: concentrations of constituents (mM): tris(hydroxymethyl)aminomethane 50; MgCl$_2$ 1; NaCl 120; KCl 5: pH 7.4). The homogenate was centrifuged for 5 minutes at 1000 g, the supernatant was saved and the pellet re-extracted. The pooled supernatants were centrifuged for 20 minutes at 12000 g, washed, and resuspended in HB. Membranes (30-80 µg) were incubated with 5 nM [$^{125}$I]α-BTX, 1 mg/mL BSA (bovine serum albumin), test drug, and either 2 mM CaCl$_2$ or 0.5 mM EGTA [ethylene glycol-bis(β-aminoethylether)] for 2 hours at 21° C., and then filtered and washed 4 times over Whatman glass fiber filters (thickness C) using a Brandel cell harvester. Pretreating the filters for 3 hours with 1% (BSA/0.01% PEI (polyethyleneimine) in water was critical for low filter blanks (0.07% of total counts per minute). Nonspecific binding was described by 100 µM (−)-nicotine, and specific binding was typically 75%.

Test B—Assay for Affinity to the α4 nAChR Subtype

[$^3$H]-(−)-nicotine binding. Using a procedure modified from Martino-Barrows and Kellar (Mol Pharm (1987) 31:169-174), rat brain (cortex and hippocampus) was homogenized as in the [$^{125}$I]α-BTX binding assay, centrifuged for 20 minutes at 12,000×g, washed twice, and then resuspended in HB containing 100 µM diisopropyl fluorophosphate. After 20 minutes at 4° C., membranes (approximately 0.5 mg) were incubated with 3 nM [$^3$H]-(−)-nicotine, test drug, 1 µM atropine, and either 2 mM CaCl$_2$ or 0.5 mM EGTA for 1 h at 4° C., and then filtered over Whatman glass fiber filters (thickness C) (pretreated for 1 h with 0.5% PEI) using a Brandel cell harvester. Nonspecific binding was described by 100 µM carbachol, and specific binding was typically 84%.

Binding Data Analysis for Tests A and B

IC$_{50}$ values and pseudo Hill coefficients (nH) were calculated using the non-linear curve-fitting program ALLFIT (DeLean A, Munson P J and Rodbard D (1977) Am. J. Physiol., 235:E97-E102). Saturation curves were fitted to a one site model, using the non-linear regression program ENZFITTER (Leatherbarrow, R. J. (1987)), yielding KD values of 1.67 and 1.70 nM for the [$^{125}$I]-α-BTX and [3H]-(−)-nicotine ligands respectively. Ki values were estimated using the general Cheng-Prusoff equation:

$$Ki = [IC_{50}]/((2+([ligand]/[KD])n)1/n - 1)$$

where a value of n=1 was used whenever nH<1.5 and a value of n=2 was used when nH≧1.5. Samples were assayed in triplicate and were typically ±5%. Ki values were determined using 6 or more drug concentrations. The compounds of the invention are compounds with binding affinities (Ki) of less than 1000 nM in either Test A or Test B, indicating that they are expected to have useful therapeutic activity.

The compounds of the invention have the advantage that they may be less toxic, be more efficacious, be longer acting, have a broader range of activity, be more potent, produce fewer side effects, are more easily absorbed or have other useful pharmacological properties.

What is claimed is:

1. A compound in accord with formula I:

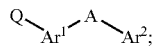

or a pharmaceutically acceptable salt thereof, wherein:
Q is a moiety of formula II

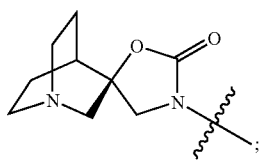

-A- is selected from —O—, —S—, or —NR$^1$—, or is a bond directly connecting Ar$^1$ and Ar$^2$;
Ar$^1$ is selected from formula III or IV:

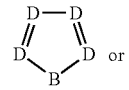

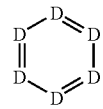

wherein B is O, S, or NR$^1$;
R$^1$ is independently at each occurrence selected from hydrogen or R$^3$;
D is independently at each occurrence selected from N or CR$^2$, provided that D is N at no more than two occurrences;
R$^2$ is independently at each occurrence selected from hydrogen, —R$^3$, —C$_2$-C$_6$alkenyl, —C$_2$-C$_6$alkynyl, halogen, —CN, —NO$_2$, —C(O)R$^4$, —S(O)$_n$R$^5$, —NR$^6$R$^7$, —OR$^8$, Q or a bond, provided that R$^2$ is Q at one occurence, and at one occurrence is a bond connecting Ar$^1$ to A, or when -A- is a bond, to Ar$^2$;
R$^3$ is selected from an unsubstituted straight-chained, branched, or cyclic C$_1$-C$_6$alkyl group, or selected from a straight-chained, branched, or cyclic C$_1$-C$_6$alkyl group substituted with up to five halogen atoms, and up to two substituents selected from: C$_2$-C$_6$alkenyl, C$_2$-C$_6$alkynyl, —CN, —C(O)R$^4$, —S(O)$_n$R$^5$, —NR$^6$R$^7$, or —OR$^8$;
R$^4$ is independently at each occurrence selected from hydrogen, R$^9$, —NR$^{10}$R$^{11}$, or —OR$^8$;
R$^5$ is independently at each occurrence selected from hydrogen, R$^9$, or —NR$^{10}$R$^{11}$;
R$^6$ and R$^7$ are independently at each occurrence selected from hydrogen, R$^9$, —C(O)R$^4$ or —S(O)$_n$R$^5$, or in combination at any one occurrence of —NR$^6$R$^7$ are (CH$_2$)$_p$G(CH$_2$)$_q$ where G is O, S, NR$^8$ or a bond;
R$^8$ is selected from hydrogen or R$^9$;
R$^9$ is selected from an unsubstituted straight-chained, branched, or cyclic C$_1$-C$_6$alkyl group, or selected from a straight-chained, branched, or cyclic C$_1$-C$_6$alkyl group substituted with up to five halogen atoms, and up to one substituent selected from: C$_2$-C$_6$ alkenyl, C$_2$-C$_6$alkynyl, —CN, —NR$^{10}$R$^{11}$—OR$^{12}$;
R$^{10}$ and R$^{11}$ are independently at each occurrence selected from hydrogen, R$^{12}$, —C(O)R$^{12}$, —S(O)$_n$R$^{12}$, or in combination at any one occurrence of —NR$^{10}$R$^{11}$ are (CH$_2$)$_p$J(CH$_2$)$_q$ where J is O, S, NH, NR$^{12}$ or a bond;
R$^{12}$ is selected from an unsubstituted straight-chained, branched, or cyclic C$_1$-C$_6$alkyl group, or selected from a straight-chained, branched, or cyclic C$_1$-C$_6$alkyl group substituted with up to five halogen atoms;
Ar$^2$ is selected from an unsubstituted 5- or 6-membered aromatic or heteroaromatic ring containing zero to two nitrogen atoms, zero to one oxygen atoms, and zero to one sulfur atoms, or selected from an 8-, 9- or 10-membered fused aromatic or heteroaromatic ring system containing zero to three nitrogen atoms, zero to one oxygen atom, and zero to one sulfur atom, or is selected from a 5- or 6-membered aromatic or heteroaromatic ring containing zero to two nitrogen atoms, zero to one oxygen atoms, and zero to one sulfur atoms, or is selected from an 8-, 9- or 10-membered fused aromatic or heteroaromatic ring system containing zero to three nitrogen atoms, zero to one oxygen atom, and zero to one sulfur atom where each foregoing $Ar^2$ moiety may bear one to three substituents selected from $R^3$, $C_2$-$C_6$alkenyl, $C_2$-$C_6$alkynyl, halogen, —CN, —NO$_2$, —C(O)R$^4$, —S(O)$_n$R$^5$, —NR$^6$R$^7$, —OR$^8$;

n at each occurrence is 0, 1, or 2;

p at each occurrence is 2, 3, or 4;

q at each occurrence is 0, 1, or 2.

2. A compound or a pharmaceutically acceptable salt thereof according to claim 1, wherein:

$Ar^1$ is selected from formula III or IV:

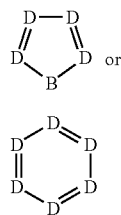

B is O, S, or NR$^1$;

$R^1$ is independently at each occurrence selected from hydrogen or $R^3$;

D is independently at each occurrence selected from N or CR$^2$, provided that D is N at two occurrences;

$R^2$ is independently at each occurrence selected from hydrogen, —R$^3$, halogen, —CN, —NO$_2$, —C(O)R$^4$, —S(O)$_n$R$^5$, —NR$^6$R$^7$, —OR$^8$, Q or a bond, provided that $R^2$ is Q at one occurrence, and at one occurrence is a bond connecting $Ar^1$ to A, or when -A- is a bond, to $Ar^2$;

$R^3$ is an unsubstituted straight-chained, branched, or cyclic $C_1$-$C_6$alkyl group, or a straight-chained, branched, or cyclic $C_1$-$C_6$alkyl group substituted with up to five halogen atoms, and up to two substituents selected from: —CN, —C(O)R$^4$, —S(O)$_n$R$^5$, —NR$^6$R$^7$, or —OR$^8$;

$R^4$, $R^5$, $R^6$, $R^7$ and $R^8$ are independently at each occurrence selected from hydrogen or $R^9$;

$R^9$ is selected from an unsubstituted straight-chained, branched, or cyclic $C_1$-$C_6$alkyl group, or is selected from a straight-chained, branched, or cyclic $C_1$-$C_6$alkyl group substituted with up to five halogen atoms, and up to one substituent selected from: —CN, —NR$^{10}$R$^{11}$R$^{12}$;

$R^{10}$ and $R^{11}$ are at each occurrence hydrogen;

$R^{12}$ is selected from an unsubstituted straight-chained, branched, or cyclic $C_1$-$C_6$alkyl group, or selected from a straight-chained, branched, or cyclic $C_1$-$C_6$alkyl group substituted with up to five halogen atoms;

-A- is selected from —O—, —S—, or —NR$^1$—, or is a bond directly connecting $Ar^1$ and $Ar^2$;

$Ar^2$ is selected from unsubstituted phenyl; 2-pyridyl, 3-pyridyl or 4-pyridyl; 2-pyrimidyl, 4-pyrimidyl or 5-pyrimidyl; 2-pyrazinyl or 3-pyrazinyl; 2-furyl or 3-furyl; 2-thiophenyl or 3-thiophenyl; 1-pyrrolyl, 2-pyrrolyl or 3-pyrrolyl; 2-quinazolyl, 4-quinazolyl or 5-quinazolyl; 2-oxazolyl, 4-oxazolyl or 5-oxazolyl; 2-imidazolyl, 4-imidazolyl or 5-imidazolyl; 1-naphthyl or 2-naphthyl; 2-quinolyl, 3-quinolyl, 4-quinolyl, 5-quinolyl, 6-quinolyl, 7-quinolyl or 8-quinolyl; 1-isoquinolyl, 3-isoquinolyl, 4-isoquinolyl; 5-isoquinolyl, 6-isoquinolyl, 7-isoquinolyl or 8-isoquinolyl; 2-benzofuranyl, 3-benzofuranyl, 4-benzofuranyl, 5-benzofuranyl, 6-benzofuranyl or 7-benzofuranyl, 2-benzo[b]thiophenyl, 3-benzo[b]thiophenyl, 4-benzo[b]thiophenyl, 5-benzo[b]thiophenyl, 6-benzo[b]thiophenyl or 7-benzo[b]thiophenyl; 2-indolyl, 3-indolyl, 4-indolyl, 5-indolyl, 6-indolyl or 7-indolyl; 2-benzoxazolyl, 4-benzoxazolyl, 5-benzoxazolyl, 6-benzoxazolyl; or 7-benzoxazolyl; 2-benzthiazolyl, 4-benzthiazolyl, 5-benzthiazolyl, 6-benzthiazolyl or 7-benzthiazolyl; or is selected from any foregoing $Ar^2$ moiety substituted with one to three substituents selected from $R^3$, $C_2$-$C_6$ alkenyl, $C_2$-$C_6$ alkynyl, halogen, —CN, —NO$_2$, —C(O) R$^4$, —S(O)$_n$R$^5$, —NR$^6$R$^7$, —OR$^8$;

n at each occurrence is 0, 1, or 2.

3. A compound, or a pharmaceutically acceptable salt thereof, according to claim 1, wherein: $R^2$ is Q at one occurrence and is a bond connecting $Ar^1$ to A at one occurrence and otherwise is hydrogen.

4. A compound, or a pharmaceutically acceptable salt thereof, according to claim 1, wherein Q and -A-$Ar^2$ are in a 1,3 relationship with one another on $Ar^1$.

5. A compound, or a pharmaceutically acceptable salt thereof, according to claim 1, wherein -A- is a bond directly connecting $Ar^1$ and $Ar^2$.

6. A compound, or a pharmaceutically acceptable salt thereof, according to claim 1, wherein $Ar^1$ is a moiety of formula III.

7. A compound, or a pharmaceutically acceptable salt thereof, according to claim 1 wherein $Ar^1$ is selected from a furan ring or a thiophene ring.

8. A compound, or a pharmaceutically acceptable salt thereof, according to claim 1, wherein $Ar^1$ is a moiety of formula III and B is selected from O or S.

9. A compound, or a pharmaceutically acceptable salt thereof, according to claim 1, wherein $Ar^1$ is a moiety of formula III and B is S.

10. A compound, or a pharmaceutically acceptable salt thereof, according to claim 1, wherein $Ar^1$ is a moiety of formula III and D is CR$^2$ where $R^2$ is Q at one occurrence and is a bond connecting $Ar^1$ to A at one occurrence and otherwise is hydrogen.

11. A compound, or a pharmaceutically acceptable salt thereof, according to claim 1, wherein $R^3$ is selected from:

methyl, ethyl, linear, cyclic or branched propyl, butyl, pentyl or hexyl, ethenyl or 1-propenyl, 2-propenyl or 3-propenyl, linear, branched or cyclic butenyl, pentenyl or hexenyl, ethynyl or propynyl, chloro, bromo, fluoro or iodo, —CN, —NO$_2$, —C(O)R$^4$, —S(O)$_n$R$^5$, —NR$^6$R$^7$ or —OR$^8$;

$R^4$ is independently at each occurrence selected from hydrogen, $R^9$, —NR$^{10}$R$^{11}$, —OR$^8$ trifluoromethyl, trifluoroethyl, methoxymethyl, trifluoromethoxymethyl, methoxyethyl or trifluoromethoxyethyl;

$R^5$ is independently at each occurrence selected from hydrogen, $R^9$, or —NR$^{10}$R$^{11}$;

$R^6$ and $R^7$ are independently at each occurrence selected from hydrogen, $R^9$, —C(O)R$^4$, —S(O)$_n$R$^5$, or in combination at any one occurrence of —NR$^6$R$^7$ are (CH$_2$)$_p$G(CH$_2$)$_q$ where G is O, S, NR$^8$ or a bond;

$R^8$ is selected from hydrogen or $R^9$;

$R^9$ is selected from methyl, ethyl, linear, cyclic or branched propyl, butyl, pentyl or hexyl ethenyl or 1-propenyl, 2-propenyl or 3-propenyl linear, branched or cyclic butenyl, pentenyl or hexenyl, ethynyl or propynyl, where any foregoing R⁹ moiety may bear up to five chloro, bromo, fluoro or iodo atoms, and up to one substituent selected from:

—CN, —NR¹⁰R¹¹—OR¹²;

R¹⁰ and R¹¹ are independently at each occurrence selected from hydrogen, R¹², —C(O)R¹², —S(O)$_n$R¹², or in combination at any one occurrence of —NR¹⁰R¹¹ are (CH₂)$_p$J(CH₂)$_q$ where J is O, S, NH, NR¹² or a bond;

R¹² is methyl, ethyl, linear, cyclic or branched propyl, butyl, pentyl or hexyl ethenyl or 1-propenyl, 2-propenyl or 3-propenyl linear, branched or cyclic butenyl, pentenyl or hexenyl, ethynyl or propynyl, where any foregoing R¹² moiety may bear up to five chloro, bromo, fluoro, iodo atoms, Ar² is selected from unsubstituted phenyl; 2-pyridyl, 3-pyridyl or 4-pyridyl; 2-pyrimidyl, 4-pyrimidyl or 5-pyrimidyl; 2-pyrazinyl or 3-pyrazinyl; 2-furyl or 3-furyl; 2-thiophenyl or 3-thiophenyl; 1-pyrrolyl, 2-pyrrolyl or 3-pyrrolyl; 2-quinazolyl, 4-quinazolyl or 5-quinazolyl; 2-oxazolyl, 4-oxazolyl or 5-oxazolyl; 2-imidazolyl, 4-imidazolyl or 5-imidazolyl; 1-naphthyl or 2-naphthyl; 2-quinolyl, 3-quinolyl, 4-quinolyl, 5-quinolyl, 6-quinolyl, 7-quinolyl or 8-quinolyl; 1-isoquinolyl, 3-isoquinolyl, 4-isoquinolyl; 5-isoquinolyl, 6-isoquinolyl, 7-isoquinolyl or 8-isoquinolyl; 2-benzofuranyl, 3-benzofuranyl, 4-benzofuranyl, 5-benzofuranyl, 6-benzofuranyl or 7-benzofuranyl, 2-benzo[b]thiophenyl, 3-benzo[b]thiophenyl, 4-benzo[b]thiophenyl, 5-benzo[b]thiophenyl, 6-benzo[b]thiophenyl or 7-benzo[b]thiophenyl; 2-indolyl, 3-indolyl, 4-indolyl, 5-indolyl, 6-indolyl or 7-indolyl; 2-benzoxazolyl, 4-benzoxazolyl, 5-benzoxazolyl, 6-benzoxazolyl; or 7-benzoxazolyl; 2-benzthiazolyl, 4-benzthiazolyl, 5-benzthiazolyl, 6-benzthiazolyl or 7-benzthiazolyl; or any foregoing Ar² moiety substituted with 1, 2 or 3 R³ substituents.

12. A compound according to claim 1, selected from:

(R)-3'-(5-phenyl-thiophen-2-yl)spiro[1-azabicyclo[2.2.2]octan-3,5'-oxazolidin]-2'-one;

(R)-3'-[5-(4-pyridyl)thiophen-2-yl]spiro[1-azabicyclo[2.2.2]octan-3,5'-oxazolidin]-2'-one;

(R)-3'-[5-(3-pyridyl)thiophen-2-yl]spiro[1-azabicyclo[2.2.2]octan-3,5'-oxazolidin]-2'-one;

(R)-3'-[5-(2-pyridyl)thiophen-2-yl]spiro[1-azabicyclo[2.2.2]octan-3,5'-oxazolidin]-2'-one;

(R)-3'-[5-(thiophen-2-yl)thiophen-2-yl]spiro[1-azabicyclo[2.2.2]octan-3,5'-oxazolidin]-2'-one;

(R)-3'-[5-(thiophen-3-yl)thiophen-2-yl]spiro[1-azabicyclo[2.2.2]octan-3,5'-oxazolidin]-2'-one;

(R)-3'-[5-(furan-2-yl)thiophen-2-yl]spiro[1-azabicyclo[2.2.2]octan-3,5'-oxazolidin]-2'-one;

(R)-3'-[5-(furan-3-yl)thiophen-2-yl]spiro[1-azabicyclo[2.2.2]octan-3,5'-oxazolidin]-2'-one;

(R)-3'-[5-(thiazol-2-yl)thiophen-2-yl]spiro[1-azabicyclo[2.2.2]octan-3,5'-oxazolidin]-2'-one;

(R)-3'-[5-(thiazol-4-yl)thiophen-2-yl]spiro[1-azabicyclo[2.2.2]octan-3,5'-oxazolidin]-2'-one;

(R)-3'-[5-(thiazol-5-yl)thiophen-2-yl]spiro[1-azabicyclo[2.2.2]octan-3,5'-oxazolidin]-2'-one;

(R)-3'-(4-phenylthiophen-2-yl)spiro[1-azabicyclo[2.2.2]octan-3,5'-oxazolidin]-2'-one;

(R)-3'-[4-(4-pyridyl)thiophen-2-yl]spiro[1-azabicyclo[2.2.2]octan-3,5'-oxazolidin]-2'-one;

(R)-3'-[4-(3-pyridyl)thiophen-2-yl]spiro[1-azabicyclo[2.2.2]octan-3,5'-oxazolidin]-2'-one;

(R)-3'-[4-(2-pyridyl)thiophen-2-yl]spiro[1-azabicyclo[2.2.2]octan-3,5'-oxazolidin]-2'-one;

(R)-3'-[4-(thiophen-2-yl)thiophen-2-yl]spiro[1-azabicyclo[2.2.2]octan-3,5'-oxazolidin]-2'-one;

(R)-3'-[4-(thiophen-3-yl)thiophen-2-yl]spiro[1-azabicyclo[2.2.2]octan-3,5'-oxazolidin]-2'-one;

(R)-3'-[4-(furan-2-yl)thiophen-2-yl]spiro[1-azabicyclo[2.2.2]octan-3,5'-oxazolidin]-2'-one;

(R)-3'-[4-(furan-3-yl)thiophen-2-yl]spiro[1-azabicyclo[2.2.2]octan-3,5'-oxazolidin]-2'-one;

(R)-3'-[4-(thiazol-2-yl)thiophen-2-yl]spiro[1-azabicyclo[2.2.2]octan-3,5'-oxazolidin]-2'-one;

(R)-3'-[4-(thiazol-4-yl)thiophen-2-yl]spiro[1-azabicyclo[2.2.2]octan-3,5'-oxazolidin]-2'-one;

(R)-3'-[4-(thiazol-5-yl)thiophen-2-yl]spiro[1-azabicyclo[2.2.2]octan-3,5'-oxazolidin]-2'-one;

(R)-3'-(2-phenylthiophen-4-yl)spiro[1-azabicyclo[2.2.2]octan-3,5'-oxazolidin]-2'-one;

(R)-3'-[2-(4-pyridyl)thiophen-4-yl]spiro[1-azabicyclo[2.2.2]octan-3,5'-oxazolidin]-2'-one;

(R)-3'-[2-(3-pyridyl)thiophen-4-yl]spiro[1-azabicyclo[2.2.2]octan-3,5'-oxazolidin]-2'-one;

(R)-3'-[2-(2-pyridyl)thiophen-4-yl]spiro[1-azabicyclo[2.2.2]octan-3,5'-oxazolidin]-2'-one;

(R)-3'-[2-(thiophen-2-yl)thiophen-4-yl]spiro[1-azabicyclo[2.2.2]octan-3,5'-oxazolidin]-2'-one;

(R)-3'-[2-(thiophen-3-yl)thiophen-4-yl]spiro[1-azabicyclo[2.2.2]octan-3,5'-oxazolidin]-2'-one;

(R)-3'-[2-(furan-2-yl)thiophen-4-yl]spiro[1-azabicyclo[2.2.2]octan-3,5'-oxazolidin]-2'-one;

(R)-3'-[2-(furan-3-yl)thiophen-4-yl]spiro[1-azabicyclo[2.2.2]octan-3,5'-oxazolidin]-2'-one;

(R)-3'-[2-(thiazol-2-yl)thiophen-4-yl]spiro[1-azabicyclo[2.2.2]octan-3,5'-oxazolidin]-2'-one;

(R)-3'-[2-(thiazol-4-yl)thiophen-4-yl]spiro[1-azabicyclo[2.2.2]octan-3,5'-oxazolidin]-2'-one;

(R)-3'-[2-(thiazol-5-yl)thiophen-4-yl]spiro[1-azabicyclo[2.2.2]octan-3,5'-oxazolidin]-2'-one;

(R)-3'-(5-phenylfuran-2-yl)spiro[1-azabicyclo[2.2.2]octan-3,5'-oxazolidin]-2'-one;

(R)-3'-[5-(4-pyridyl)furan-2-yl]spiro[1-azabicyclo[2.2.2]octan-3,5'-oxazolidin]-2'-one;

(R)-3'-[5-(3-pyridyl)furan-2-yl]spiro[1-azabicyclo[2.2.2]octan-3,5'-oxazolidin]-2'-one;

(R)-3'-[5-(2-pyridyl)furan-2-yl]spiro[1-azabicyclo[2.2.2]octan-3,5'-oxazolidin]-2'-one;

(R)-3'-[5-(thiophen-2-yl)furan-2-yl]spiro[1-azabicyclo[2.2.2]octan-3,5'-oxazolidin]-2'-one;

(R)-3'-[5-(thiophen-3-yl)furan-2-yl]spiro[1-azabicyclo[2.2.2]octan-3,5'-oxazolidin]-2'-one;

(R)-3'-[5-(furan-2-yl)furan-2-yl]spiro[1-azabicyclo[2.2.2]octan-3,5'-oxazolidin]-2'-one;

(R)-3'-[5-(furan-3-yl)furan-2-yl]spiro[1-azabicyclo[2.2.2]octan-3,5'-oxazolidin]-2'-one;

(R)-3'-[5-(thiazol-2-yl)furan-2-yl]spiro[1-azabicyclo[2.2.2]octan-3,5'-oxazolidin]-2'-one;

(R)-3'-[5-(thiazol-4-yl)furan-2-yl]spiro[1-azabicyclo[2.2.2]octan-3,5'-oxazolidin]-2'-one;

(R)-3'-[5-(thiazol-5-yl)furan-2-yl]spiro[1-azabicyclo[2.2.2]octan-3,5'-oxazolidin]-2'-one;

(R)-3'-(4-phenylfuran-2-yl)spiro[1-azabicyclo[2.2.2]octan-3,5'-oxazolidin]-2'-one;

(R)-3'-[4-(4-pyridyl)furan-2-yl]spiro[1-azabicyclo[2.2.2]octan-3,5'-oxazolidin]-2'-one;

(R)-3'-[4-(3-pyridyl)furan-2-yl]spiro[1-azabicyclo[2.2.2]octan-3,5'-oxazolidin]-2'-one;

(R)-3'-[4-(2-pyridyl)furan-2-yl]spiro[1-azabicyclo[2.2.2]octan-3,5'-oxazolidin]-2'-one;
(R)-3'-[4-(thiophen-2-yl)furan-2-yl]spiro[1-azabicyclo[2.2.2]octan-3,5'-oxazolidin]-2'-one;
(R)-3'-[4-(thiophen-3-yl)furan-2-yl]spiro[1-azabicyclo[2.2.2]octan-3,5'-oxazolidin]-2'-one;
(R)-3'-[4-(furan-2-yl)furan-2-yl]spiro[1-azabicyclo[2.2.2]octan-3,5'-oxazolidin]-2'-one;
(R)-3'-[4-(furan-3-yl)furan-2-yl]spiro[1-azabicyclo[2.2.2]octan-3,5'-oxazolidin]-2'-one;
(R)-3'-[4-(thiazol-2-yl)furan-2-yl]spiro[1-azabicyclo[2.2.2]octan-3,5'-oxazolidin]-2'-one;
(R)-3'-[4-(thiazol-4-yl)furan-2-yl]spiro[1-azabicyclo[2.2.2]octan-3,5'-oxazolidin]-2'-one;
(R)-3'-[4-(thiazol-5-yl)furan-2-yl]spiro[1-azabicyclo[2.2.2]octan-3,5'-oxazolidin]-2'-one;
(R)-3'-(2-phenylfuran-4-yl)spiro[1-azabicyclo[2.2.2]octan-3,5'-oxazolidin]-2'-one;
(R)-3'-[2-(4-pyridyl)furan-4-yl]spiro[1-azabicyclo[2.2.2]octan-3,5'-oxazolidin]-2'-one;
(R)-3'-[2-(3-pyridyl)furan-4-yl]spiro[1-azabicyclo[2.2.2]octan-3,5'-oxazolidin]-2'-one;
(R)-3'-[2-(2-pyridyl)furan-4-yl]spiro[1-azabicyclo[2.2.2]octan-3,5'-oxazolidin]-2'-one;
(R)-3'-[2-(thiophen-2-yl)furan-4-yl]spiro[1-azabicyclo[2.2.2]octan-3,5'-oxazolidin]-2'-one;
(R)-3'-[2-(thiophen-3-yl)furan-4-yl]spiro[1-azabicyclo[2.2.2]octan-3,5'-oxazolidin]-2'-one;
(R)-3'-[2-(furan-2-yl)furan-4-yl]spiro[1-azabicyclo[2.2.2]octan-3,5'-oxazolidin]-2'-one;
(R)-3'-[2-(furan-3-yl)furan-4-yl]spiro[1-azabicyclo[2.2.2]octan-3,5'-oxazolidin]-2'-one;
(R)-3'-[2-(thiazol-2-yl)furan-4-yl]spiro[1-azabicyclo[2.2.2]octan-3,5'-oxazolidin]-2'-one;
(R)-3'-[2-(thiazol-4-yl)furan-4-yl]spiro[1-azabicyclo[2.2.2]octan-3,5'-oxazolidin]-2'-one, or
(R)-3'-[2-(thiazol-5-yl)furan-4-yl]spiro[1-azabicyclo[2.2.2]octan-3,5'-oxazolidin]-2'-one, or a pharmaceutically-acceptable salt thereof.

13. A compound according to claim 1, selected from:
(R)-3'-{5-[3-(N,N-dimethylcarbamoyl)phenyl]thiophen-2-yl}spiro[1-azabicyclo[2.2.2]octan-3,5'-oxazolidin]-2'-one;
(R)-3'-{5-[3-(N,N-diethylcarbamoyl)phenyl]thiophen-2-yl}spiro[1-azabicyclo[2.2.2]octan-3,5'-oxazolidin]-2'-one;
(R)-3'-{5-[3-(pyrrolidine-1-carbonyl)phenyl]thiophen-2-yl}spiro[1-azabicyclo[2.2.2]octan-3,5'-oxazolidin]-2'-one;
(R)-3'-{5-[3-(piperidine-1-carbonyl)phenyl]thiophen-2-yl}spiro[1-azabicyclo[2.2.2]octan-3,5'-oxazolidin]-2'-one;
(R)-3'-{5-[3-(morpholine-4-carbonyl)phenyl]thiophen-2-yl}spiro[1-azabicyclo[2.2.2]octan-3,5'-oxazolidin]-2'-one;
(R)-3'-[5-(3-aminophenyl)thiophen-2-yl]spiro[1-azabicyclo[2.2.2]octan-3,5'-oxazolidin]-2'-one;
(R)-3'-{5-[3-(N,N-dimethylamino)phenyl]thiophen-2-yl}spiro[1-azabicyclo[2.2.2]octan-3,5'-oxazolidin]-2'-one;
(R)-3'-{5-[3-(propionylamino)phenyl]thiophen-2-yl]spiro[1-azabicyclo[2.2.2]octan-3,5'-oxazolidin]-2'-one;
(R)-3'-{5-[3-(butyrylamino)phenyl]thiophen-2-yl]spiro[1-azabicyclo[2.2.2]octan-3,5'-oxazolidin]-2'-one;
(R)-3'-{5-[3-(benzoylamino)phenyl]thiophen-2-yl]spiro[1-azabicyclo[2.2.2]octan-3,5'-oxazolidin]-2'-one;
(R)-3'-{5-[3-(2-propoxy)phenyl]thiophen-2-yl}spiro[1-azabicyclo[2.2.2]octan-3,5'-oxazolidin]-2'-one;
(R)-3'-[5-(3-trifluoromethoxyphenyl)thiophen-2-yl]spiro[1-azabicyclo[2.2.2]octan-3,5'-oxazolidin]-2'-one;
(R)-3'-[5-(quinolin-2-yl)thiophen-2-yl]spiro[1-azabicyclo[2.2.2]octan-3,5'-oxazolidin]-2'-one;
(R)-3'-[5-(quinolin-3-yl)thiophen-2-yl]spiro[1-azabicyclo[2.2.2]octan-3,5'-oxazolidin]-2'-one;
(R)-3'-[5-(quinolin-4-yl)thiophen-2-yl]spiro[1-azabicyclo[2.2.2]octan-3,5'-oxazolidin]-2'-one;
(R)-3'-[5-(quinolin-5-yl)thiophen-2-yl]spiro[1-azabicyclo[2.2.2]octan-3,5'-oxazolidin]-2'-one;
(R)-3'-[5-(quinolin-6-yl)thiophen-2-yl]spiro[1-azabicyclo[2.2.2]octan-3,5'-oxazolidin]-2'-one;
(R)-3'-[5-(quinolin-7-yl)thiophen-2-yl]spiro[1-azabicyclo[2.2.2]octan-3,5'-oxazolidin]-2'-one;
(R)-3'-[5-(quinolin-8-yl)thiophen-2-yl]spiro[1-azabicyclo[2.2.2]octan-3,5'-oxazolidin]-2'-one;
(R)-3'-[5-(pyrimidin-2-yl)thiophen-2-yl]spiro[1-azabicyclo[2.2.2]octan-3,5'-oxazolidin]-2'-one;
(R)-3'-[5-(pyrimidin-4-yl)thiophen-2-yl]spiro[1-azabicyclo[2.2.2]octan-3,5'-oxazolidin]-2'-one;
(R)-3'-[5-(pyrimidin-5-yl)thiophen-2-yl]spiro[1-azabicyclo[2.2.2]octan-3,5'-oxazolidin]-2'-one;
(R)-3'-(2-phenylthiazol-4-yl)spiro[1-azabicyclo[2.2.2]octan-3,5'-oxazolidin]-2'-one;
(R)-3'-[2-(2-pyridyl)thiazol-4-yl]spiro[1-azabicyclo[2.2.2]octan-3,5'-oxazolidin]-2'-one;
(R)-3'-[2-(3-pyridyl)thiazol-4-yl]spiro[1-azabicyclo[2.2.2]octan-3,5'-oxazolidin]-2'-one;
(R)-3'-[2-(4-pyridyl)thiazol-4-yl]spiro[1-azabicyclo[2.2.2]octan-3,5'-oxazolidin]-2'-one;
(R)-3'-(2-phenylthiazol-5-yl)spiro[1-azabicyclo[2.2.2]octan-3,5'-oxazolidin]-2'-one;
(R)-3'-[2-(2-pyridyl)thiazol-5-yl]spiro[1-azabicyclo[2.2.2]octan-3,5'-oxazolidin]-2'-one;
(R)-3'-[2-(3-pyridyl)thiazol-5-yl]spiro[1-azabicyclo[2.2.2]octan-3,5'-oxazolidin]-2'-one;
(R)-3'-[2-(4-pyridyl)thiazol-5-yl]spiro[1-azabicyclo[2.2.2]octan-3,5'-oxazolidin]-2'-one;
(R)-3'-[5-(2-pyridyl)-1,3,4-thiadiazol-2-yl]spiro[1-azabicyclo[2.2.2]octan-3,5'-oxazolidin]-2'-one;
(R)-3'-[5-(3-pyridyl)-1,3,4-thiadiazol-2-yl]spiro[1-azabicyclo[2.2.2]octan-3,5'-oxazolidin]-2'-one;
(R)-3'-(5-phenyl-1,3,4-oxadiazol-2-yl)spiro[1-azabicyclo[2.2.2]octan-3,5'-oxazolidin]-2'-one;
(R)-3'-(5-phenyloxazol-2-yl)spiro[1-azabicyclo[2.2.2]octan-3,5'-oxazolidin]-2'-one;
(R)-3'-[5-(2-pyridyl)oxazol-2-yl]spiro[1-azabicyclo[2.2.2]octan-3,5'-oxazolidin]-2'-one;
(R)-3'-[5-(3-pyridyl)thiazol-2-yl]spiro[1-azabicyclo[2.2.2]octan-3,5'-oxazolidin]-2'-one;
(R)-3'-[5-(4-pyridyl)thiazol-2-yl]spiro[1-azabicyclo[2.2.2]octan-3,5'-oxazolidin]-2'-one;
(R)-3'-(4-phenyloxazol-2-yl)spiro[1-azabicyclo[2.2.2]octan-3,5'-oxazolidin]-2'-one;
(R)-3'-[4-(2-pyridyl)oxazol-2-yl]spiro[1-azabicyclo[2.2.2]octan-3,5'-oxazolidin]-2'-one;
(R)-3'-[4-(3-pyridyl)thiazol-2-yl]spiro[1-azabicyclo[2.2.2]octan-3,5'-oxazolidin]-2'-one;
(R)-3'-[4-(4-pyridyl)thiazol-2-yl]spiro[1-azabicyclo[2.2.2]octan-3,5'-oxazolidin]-2'-one;
(R)-3'-(2-phenyloxazol-4-yl)spiro[1-azabicyclo[2.2.2]octan-3,5'-oxazolidin]-2'-one;
(R)-3'-[2-(2-pyridyl)oxazol-4-yl]spiro[1-azabicyclo[2.2.2]octan-3,5'-oxazolidin]-2'-one;

(R)-3'-[2-(3-pyridyl)thiazol-4-yl]spiro[1-azabicyclo[2.2.2]octan-3,5'-oxazolidin]-2'-one;
(R)-3'-[2-(4-pyridyl)thiazol-4-yl]spiro[1-azabicyclo[2.2.2]octan-3,5'-oxazolidin]-2'-one;
(R)-3'-(2-phenyloxazol-5-yl)spiro[1-azabicyclo[2.2.2]octan-3,5'-oxazolidin]-2'-one;
(R)-3'-[2-(2-pyridyl)oxazol-5-yl]spiro[1-azabicyclo[2.2.2]octan-3,5'-oxazolidin]-2'-one;
(R)-3'-[2-(3-pyridyl)thiazol-5-yl]spiro[1-azabicyclo[2.2.2]octan-3,5'-oxazolidin]-2'-one;
(R)-3'-[2-(4-pyridyl)thiazol-5-yl]spiro[1-azabicyclo[2.2.2]octan-3,5'-oxazolidin]-2'-one;
(R)-3'-[5-(2-pyridyl)-1,3,4-oxadiazol-2-yl]spiro[1-azabicyclo[2.2.2]octan-3,5'-oxazolidin]-2'-one;
(R)-3'-[5-(3-pyridyl)-1,3,4-oxadiazol-2-yl]spiro[1-azabicyclo[2.2.2]octan-3,5'-oxazolidin]-2'-one; and
(R)-3'-[5-(4-pyridyl)-1,3,4-oxadiazol-2-yl]spiro[1-azabicyclo[2.2.2]octan-3,5'-oxazolidin]-2'-one; or a pharmaceutically acceptable salt thereof.

14. A compound according to claim 1, selected from:
(R)-3'-[5-(2-fluorophenyl)thiophen-2-yl]spiro[1-azabicyclo[2.2.2]octan-3,5'-oxazolidin]-2'-one;
(R)-3'-[5-(3-fluorophenyl)thiophen-2-yl]spiro[1-azabicyclo[2.2.2]octan-3,5'-oxazolidin]-2'-one;
(R)-3'-[5-(4-fluorophenyl)thiophen-2-yl]spiro[1-azabicyclo[2.2.2]octan-3,5'-oxazolidin]-2'-one;
(R)-3'-[5-(2-chlorophenyl)thiophen-2-yl]spiro[1-azabicyclo[2.2.2]octan-3,5'-oxazolidin]-2'-one;
(R)-3'-[5-(3-chlorophenyl)thiophen-2-yl]spiro[1-azabicyclo[2.2.2]octan-3,5'-oxazolidin]-2'-one;
(R)-3'-[5-(4-chlorophenyl)thiophen-2-yl]spiro[1-azabicyclo[2.2.2]octan-3,5'-oxazolidin]-2'-one;
(R)-3'-[5-(3,4-dichlorophenyl)thiophen-2-yl]spiro[1-azabicyclo[2.2.2]octan-3,5'-oxazolidin]-2'-one;
(R)-3'-[5-(3-methylphenyl)thiophen-2-yl]spiro[1-azabicyclo[2.2.2]octan-3,5'-oxazolidin]-2'-one;
(R)-3'-[5-(4-methylphenyl)thiophen-2-yl]spiro[1-azabicyclo[2.2.2]octan-3,5'-oxazolidin]-2'-one;
(R)-3'-[5-(3-methoxyphenyl)thiophen-2-yl]spiro[1-azabicyclo[2.2.2]octan-3,5'-oxazolidin]-2'-one;
(R)-3'-[5-(4-methoxyphenyl)thiophen-2-yl]spiro[1-azabicyclo[2.2.2]octan-3,5'-oxazolidin]-2'-one;
(R)-3'-[5-(3-methoxyphenyl)thiophen-2-yl]spiro[1-azabicyclo[2.2.2]octan-3,5'-oxazolidin]-2'-one;
(R)-3'-[5-(3-trifluoromethylphenyl)thiophen-2-yl]spiro[1-azabicyclo[2.2.2]octan-3,5'-oxazolidin]-2'-one;
(R)-3'-[5-(4-trifluoromethylphenyl)thiophen-2-yl]spiro[1-azabicyclo[2.2.2]octan-3,5'-oxazolidin]-2'-one;
(R)-3'-[5-(3-trifluoromethoxyphenyl)thiophen-2-yl]spiro[1-azabicyclo[2.2.2]octan-3,5'-oxazolidin]-2'-one;
(R)-3'-[5-(4-trifluoromethoxyphenyl)thiophen-2-yl]spiro[1-azabicyclo[2.2.2]octan-3,5'-oxazolidin]-2'-one;
(R)-3'-[5-(naphthalen-2-yl)thiophen-2-yl]spiro[1-azabicyclo[2.2.2]octan-3,5'-oxazolidin]-2'-one;
(R)-3'-[5-(benzofuran-2-yl)thiophen-2-yl]spiro[1-azabicyclo[2.2.2]octan-3,5'-oxazolidin]-2'-one;
(R)-3'-[5-(benzo[b]thiophen-2-yl)thiophen-2-yl]spiro[1-azabicyclo[2.2.2]octan-3,5'-oxazolidin]-2'-one;
(R)-3'-[5-(2-fluoropyridin-3-yl)thiophen-2-yl]spiro[1-azabicyclo[2.2.2]octan-3,5'-oxazolidin]-2'-one;
(R)-3'-[5-(2-chloropyridin-3-yl)thiophen-2-yl]spiro[1-azabicyclo[2.2.2]octan-3,5'-oxazolidin]-2'-one;
(R)-3'-[5-(2-methoxypyridin-3-yl)thiophen-2-yl]spiro[1-azabicyclo[2.2.2]octan-3,5'-oxazolidin]-2'-one;
(R)-3'-[5-(2-aminopyridin-3-yl)thiophen-2-yl]spiro[1-azabicyclo[2.2.2]octan-3,5'-oxazolidin]-2'-one;
(R)-3'-{5-[2-(N,N-dimethylamino)pyridin-3-yl]thiophen-2-yl}spiro[1-azabicyclo[2.2.2]octan-3,5'-oxazolidin]-2'-one;
(R)-3'-[5-(5-chloropyridin-3-yl)thiophen-2-yl]spiro[1-azabicyclo[2.2.2]octan-3,5'-oxazolidin]-2'-one;
(R)-3'-[5-(5-methoxypyridin-3-yl)thiophen-2-yl]spiro[1-azabicyclo[2.2.2]octan-3,5'-oxazolidin]-2'-one;
(R)-3'-[5-(5-aminopyridin-3-yl)thiophen-2-yl]spiro[1-azabicyclo[2.2.2]octan-3,5'-oxazolidin]-2'-one; and
(R)-3'-{5-[5-(N,N-dimethylamino)pyridin-3-yl]thiophen-2-yl}spiro[1-azabicyclo[2.2.2]octan-3,5'-oxazolidin]-2'-one; or a pharmaceutically acceptable salt thereof.

15. A compound, or a pharmaceutically acceptable salt thereof, according to claim 1, wherein one or more of the atoms of said compound is a radioisotope of said atom.

16. A compound, or a pharmaceutically acceptable salt thereof, according to claim 15, wherein the radioisotope is tritium.

17. A method for the discovery of novel medicinal compounds which bind to and modulate the activity, by agonism, partial agonism, or antagonism, of the α7 nicotinic acetylcholine receptor comprising measuring the displacement of a compound according to claim 15 from an α7 nicotinic acetylcholine receptor.

18. A pharmaceutical composition comprising a compound according to claim 1, an enantiomer thereof or a pharmaceutically-acceptable salt thereof, and a pharmaceutically-acceptable diluent or carrier.

* * * * *